United States Patent [19]

Doria et al.

[11] Patent Number: 4,609,660
[45] Date of Patent: * Sep. 2, 1986

[54] SUBSTITUTED CARBOXY-THIAZOLO[3,2-A]PYRIMIDINE DERIVATIVES

[75] Inventors: Gianfederico Doria, Milan; Carlo Passarotti, Gallarate; Maria L. Corno, Milan, all of Italy

[73] Assignee: Farmitalia Carlo Erba, S.p.A., Milan, Italy

[*] Notice: The portion of the term of this patent subsequent to Dec. 10, 2002 has been disclaimed.

[21] Appl. No.: 747,436

[22] Filed: Jun. 21, 1985

Related U.S. Application Data

[62] Division of Ser. No. 569,693, Jan. 11, 1985, Pat. No. 4,558,046.

[30] Foreign Application Priority Data

Jan. 12, 1983 [GB] United Kingdom ............... 8300728

[51] Int. Cl.⁴ .................. A61K 31/505; C07D 513/02
[52] U.S. Cl. .................... 514/258; 544/117; 544/278
[58] Field of Search ............... 544/278, 117; 514/258

[56] References Cited

U.S. PATENT DOCUMENTS

| | | | |
|---|---|---|---|
| 3,888,983 | 6/1975 | Baetz | 544/278 |
| 4,168,380 | 9/1979 | Le Mahieu | 544/250 |
| 4,310,526 | 1/1982 | Doria et al. | 544/252 |
| 4,419,356 | 12/1983 | Debarre et al. | 544/278 |
| 4,444,773 | 4/1984 | Doria et al. | 544/281 |

FOREIGN PATENT DOCUMENTS 1334628 10/1973 United Kingdom ............... 544/278

*Primary Examiner*—Donald G. Daus
*Assistant Examiner*—Stephen M. Kapner
*Attorney, Agent, or Firm*—Murray and Whisenhunt

[57] ABSTRACT

Carboxy-thiazolo[3,2-a]pyrimidine derivatives, and pharmaceutical compositions containing them. The compounds and compositions possess anti-allergic activity.

6 Claims, No Drawings

SUBSTITUTED CARBOXY-THIAZOLO[3,2-A]PYRIMIDINE DERIVATIVES

This is a divisional application of Ser. No. 569,693, filed Jan. 11, 1985, now U.S. Pat. No. 4,558,046.

The present invention relates to new carboxy-thiazolo[3,2-a] pyrimidine derivatives, to a process for their preparation and to pharmaceutical compositions containing them. The invention provides compounds having the following general formula (I)

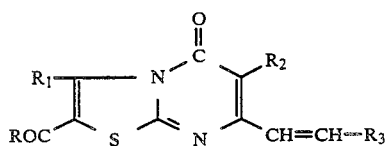

(I)

wherein
R is
(a) hydroxy;
(b) a $C_1$–$C_6$ alkoxy group unsubstituted or substituted by an unsubstituted pyridyl ring or by a

group, wherein each of $R_4$ and $R_5$ independently is a hydrogen atom or a $C_1$–$C_6$ alkyl group, or $R_4$ and $R_5$, taken together with the nitrogen atom to which they are linked, form an unsubstituted piperidino or N-pyrrolidinyl ring, or a morpholino ring unsubstituted or substituted by one or two $C_1$–$C_4$ alkyl groups, or a N-piperazinyl ring unsubstituted or substituted by a substituent chosen from $C_1$–$C_6$ alkyl, pyridyl and phenyl;
(c)

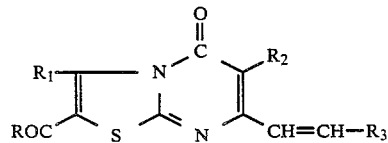

(I)

wherein $R_4$ and $R_5$ are as defined above;
(d)

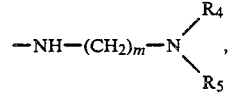

wherein m is 1, 2 or 3 and $R_4$ and $R_5$ are as defined above; or
(e) —$NR_6$—$(CH_2)_n$—$R_7$, wherein $R_6$ is hydrogen or $C_1$–$C_6$ alkyl, n is zero, 1, 2 or 3 and $R_7$ is an unsaturated heterocyclic ring containing one or more heteroatoms chosen from nitrogen and sulphur, unsubstituted or substituted by one or two substituents chosen from halogen, $C_1$–$C_6$ alkyl and $C_1$–$C_6$ alkoxy;
$R_1$ is a hydrogen atom, $C_1$–$C_6$ alkyl, an unsubstituted pyridyl ring or a phenyl ring unsubstituted or substituted by one or two substituents chosen from halogen, $C_1$–$C_6$ alkyl and $C_1$–$C_6$ alkoxy;
$R_2$ is a hydrogen or a halogen atom or a $C_1$–$C_4$ alkyl group;
$R_3$ is a thienyl or pyridyl ring, each of which unsubstituted or substituted by $C_1$–$C_6$ alkyl; or $R_3$ is a group of formula

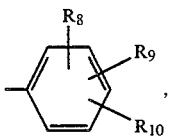

wherein each of $R_8$, $R_9$ and $R_{10}$ independently represents hydrogen, halogen, hydroxy, formyloxy, $C_2$–$C_4$ alkanoyloxy, nitro, amino, formylamino, $C_2$–$C_4$ alkanoylamino, trihalo-$C_1$–$C_6$-alkyl or a —$(O)_p$—$R_{11}$ group, wherein p is zero or 1 and $R_{11}$ represents a $C_1$–$C_6$ alkyl or $C_3$–$C_4$ alkenyl group, and the pharmaceutically acceptable salts thereof.

The invention includes within its scope also all the possible isomers (e.g. cis or trans isomers or optical isomers) and the mixtures thereof. Preferably the group —CH=CH—$R_3$ is in the trans configuration.

The alkyl, alkenyl, alkoxy, alkenyloxy, alkanoyloxy and alkanoylamino groups may be branched or straight chain groups.

When R is an unsubstituted $C_1$–$C_6$ alkoxy, it is preferably $C_1$–$C_4$ alkoxy, in particular, methoxy, ethoxy, isopropoxy, and n-butoxy.

When R is $C_1$–$C_6$ alkoxy substituted by a

group, it is for example $C_1$–$C_4$ alkoxy substituted by a substituent chosen from di($C_1$–$C_4$ alkyl)amino, morpholino unsubstituted or substituted by a methyl group and piperidino; preferably it is $C_1$–$C_2$ alkoxy substituted by di($C_1$–$C_2$alkyl)amino or by morpholino or by piperidino.

When $R_4$ and/or $R_5$ are $C_1$–$C_6$ alkyl, the alkyl group is preferably $C_1$–$C_4$ alkyl, in particular methyl, ethyl, isopropyl and t.-butyl.

When a

group is a N-piperazinyl ring substituted by a $C_1$–$C_6$ alkyl group, the alkyl group is preferably a $C_1$–$C_4$ alkyl group, in particular methyl, ethyl or propyl.

When a

group is a morpholino ring substituted by one or two $C_1-C_4$ alkyl groups, each alkyl group is preferably methyl.

When $R_7$ is an unsaturated heterocyclic ring as defined above, it may be a heteromonocyclic or a heterobicyclic ring; preferably it is a heteromonocyclic ring, in particular a pyridyl, thiazolyl and tetrazolyl ring; said ring, when substituted, is preferably substituted by one or two substituents chosen from chlorine, methyl and methoxy.

$R_1$ is preferably hydrogen, methyl, pyridyl or phenyl, wherein the phenyl ring is unsubstituted or substituted by one or two substituents chosen from methyl, chlorine and methoxy.

When $R_2$ is $C_1-C_4$ alkyl, it is preferably methyl or ethyl. When $R_2$ is a halogen atom, it is preferably chlorine or bromine.

When $R_3$ is substituted thienyl or pyridyl it is preferably substituted by $C_1-C_4$ alkyl, in particular methyl or ethyl.

Preferably $R_8$, $R_9$ and $R_{10}$ are independently selected from the group consisting of hydrogen; chlorine; fluorine; $C_1-C_4$ alkoxy, in particular methoxy or ethoxy; and $C_1-C_4$ alkyl, in particular methyl and ethyl.

When one or more of $R_8$, $R_9$ and $R_{10}$ is trihalo-$C_1-C_6$ alkyl, it is for example, trifluoro-$C_1-C_6$ alkyl, preferably trifluoro-$C_1-C_4$ alkyl, in particular trifluoromethyl. A $C_2-C_4$ alkanoyloxy group is preferably an acetoxy or propionyloxy group.

A $C_2-C_4$ alkanoylamino group is preferably an acetylamino or propionylamino group.

Preferred compounds of the invention are the compounds of formula (I) wherein

R is hydroxy, $C_1-C_4$ alkoxy, di($C_1-C_2$alkyl)aminoethoxy, piperidinoethoxy, morpholino, morpholinoethoxy, pyridylmethoxy, pyridylmethylamino, pyridylamino, thiazolylamino or tetrazolylamino;

$R_1$ is hydrogen, $C_1-C_2$ alkyl, pyridyl or phenyl;
$R_2$ is hydrogen, chlorine, bromine or $C_1-C_3$ alkyl; and
$R_3$ is
 (a″) a phenyl group unsubstituted or substituted by one or two substituents chosen from the group including fluorine, chlorine, $C_1-C_4$ alkyl, and $C_1-C_4$ alkoxy;
 (b″) a thienyl or pyridyl group, each of which unsubstituted or substituted by a methyl group; and the pharmaceutically acceptable salts thereof.

Examples of pharmaceutically acceptable salts are either those with inorganic bases, such as sodium, potassium, calcium and aluminium hydroxides or with organic bases, such as lysine, triethylamine, triethanolamine, dibenzylamine, methylbenzylamine, di-(2-ethylhexyl)-amine, piperidine, N-ethylpiperidine, N,N-diethylaminoethylamine, N-ethylmorpholine,β-phenethylamine, N-benzyl-β-phenethylamine, N-benzyl-N,N-dimethylamine and the other acceptable organic amines, or the salts with inorganic, e.g. hydrochloric, hydrobromic and sulphuric acids and with organic acids, e.g. citric, tartaric, maleic, malic, fumaric, methanesulphonic and ethanesulphonic acids. Preferred salts are the sodium and the potassium salts, as well as the hydrochlorides of the basic esters, e.g. the diethylaminoethyl and dimethylaminoethyl esters. Examples of particularly preferred compounds of the invention are:

6-chloro-7-trans-(2-phenyl-ethenyl)-5-oxo-5H-thiazolo[3,2-a]pyrimidine-2-carboxylic acid;
6-methyl-7-trans-[2-(2-methyl-phenyl)-ethenyl]-5-oxo-5H-thiazolo[3,2-a]pyrimidine-2-carboxylic acid;
6-methyl-7-trans-[2-(4-methyl-phenyl)-ethenyl]-5-oxo-5H-thiazolo[3,2-a]pyrimidine-2-carboxylic acid;
6-methyl-7-trans-[2-(3-pyridyl)-ethenyl]-5-oxo-5H-thiazolo[3,2-a]pyrimidine-2-carboxylic acid;
6-methyl-7-trans-[2-(3-methyl-phenyl)-ethenyl]-5-oxo-5H-thiazolo[3,2-a]pyrimidine-2-carboxylic acid;
6-methyl-7-trans-[2-(4-ethoxy-phenyl)-ethenyl]-5-oxo-5H-thiazolo[3,2-a]pyrimidine-2-carboxylic acid;
6-chloro-7-trans-[2-(3-methyl-phenyl)-ethenyl]-5-oxo-5H-thiazolo[3,2-a]pyrimidine-2-carboxylic acid;
6-chloro-7-trans-[2-(2-methyl-phenyl)-ethenyl]-5-oxo-5H-thiazolo[3,2-a]pyrimidine-2-carboxylic acid;
6-chloro-7-trans-[2-(2,4-dimethyl-phenyl)-ethenyl]-5-oxo-5H-thiazolo[3,2-a]pyrimidine-2-carboxylic acid;
6-chloro-3-phenyl-7-trans-(2-phenyl-ethenyl)-5-oxo-5H-thiazolo[3,2-a]pyrimidine-2-carboxylic acid;
6-chloro-3-methyl-7-trans-(2-phenyl-ethenyl)-5-oxo-5H-thiazolo[3,2-a]pyrimidine-2-carboxylic acid;
6-chloro-7-trans-[2-(4-methyl-phenyl)-ethenyl]-5-oxo-5H-thiazolo[3,2-a]pyrimidine-2-carboxylic acid;
6-chloro-7-trans-[2-(4-fluoro-phenyl)-ethenyl]-5-oxo-5H-thiazolo[3,2-a]pyrimidine-2-carboxylic acid;
6-bromo-7-trans-(2-phenyl-ethenyl)-5-oxo-5H-thiazolo[3,2-a]pyrimidine-2-carboxylic acid;
6-chloro-7-trans-[2-(2-methoxy-3-ethoxy-phenyl)-ethenyl]-5-oxo-5H-thiazolo[3,2-a]pyrimidine-2-carboxylic acid;
6-chloro-7-trans-[2-(2,5-dimethyl-phenyl)-ethenyl]-5-oxo-5H-thiazolo[3,2-a]pyrimidine-2-carboxylic acid;
6-chloro-7-trans-[2-(4-chloro-phenyl)-ethenyl]-5-oxo-5H-thiazolo[3,2-a]pyrimidine-2-carboxylic acid;
6-methyl-7-trans-[2-(2,4-dimethyl-phenyl)-ethenyl]-5-oxo-5H-thiazolo[3,2-a]pyrimidine-2-carboxylic acid;
6-methyl-7-trans-[2-(2-methoxy-3-ethoxy-phenyl)-ethenyl]-5-oxo-5H-thiazolo[3,2-a]pyrimidine-2-carboxylic acid;
6-methyl-7-trans-[2-(2,5-dimethyl-phenyl)-ethenyl]-5-oxo-5H-thiazolo[3,2-a]pyrimidine-2-carboxylic acid;
6-methyl-7-trans-[2-(2,6-dichloro-phenyl)-ethenyl]-5-oxo-5H-thiazolo[3,2-a]pyrimidine-2-carboxylic acid;
6-methyl-7-trans-[2-(4-chloro-phenyl)-ethenyl]-5-oxo-5H-thiazolo[3,2-a]pyrimidine-2-carboxylic acid;
and the pharmaceutically acceptable salts thereof, in particular the sodium salts of the carboxylic acids, and the $C_1-C_4$ alkyl esters, in particular the ethyl, isopropyl and butyl esters, and the di($C_1-C_2$)alkylaminoethyl esters.

The compounds of the invention can be prepared by a process comprising:
 (a) reacting a compound of formula (II)

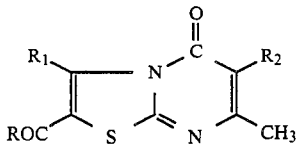

wherein R, $R_1$ and $R_2$ are as defined above or a salt thereof, with an aldehyde of formula (III)

wherein $R_3$ is as defined above; or (b) reacting a compound of formula (IV)

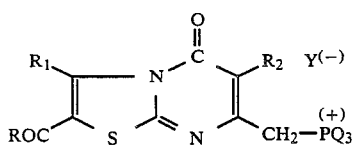

wherein R, $R_1$ and $R_2$ are as defined above, Q is aryl or $C_1-C_6$ alkyl and $Y^{(-)}$ represents an acidic anion with an aldehyde of formula (III) as defined above; or (c) reacting a compound of formula (V)

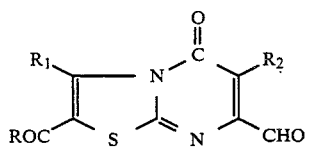

wherein R, $R_1$ and $R_2$ are as defined above, with a compound of formula (VI)

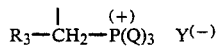

wherein Q, $R_3$ and $Y^{(-)}$ are as defined above, or alternatively with a compound of formula (VII)

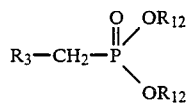

wherein $R_3$ is as defined above and $R_{12}$ is $C_1-C_4$ alkyl; and, if desired, converting a compound of formula (I) into another compound of formula (I) and/or if desired, converting a compound of formula (I) into a pharmaceutically acceptable salt and/or, if desired, obtaining a free compound of formula (I) from a salt thereof and/or, if desired, separating a mixture of isomers into the single isomers.

The acidic anion $Y^{(-)}$ in the compounds of formula (IV) and (VI) is, for example, an acidic anion derived from a hydrohalic acid, preferably derived from hydrochloric or hydrobromic acid.

When Q in the compounds of formula (IV) and (VI) is aryl, it is preferably phenyl; and when Q is $C_1-C_6$ alkyl, it is preferably ethyl.

Preferred salts of a compound of formula (II) are, for example, those with inorganic bases such as sodium, potassium and calcium salts as well as the salts with inorganic acid such as hydrochloric, hydrobromic and sulphuric acids.

The reaction of a compound of formula (II) or a salt thereof with an aldehyde of formula (III) is preferably carried out in the presence of a basic condensing agent such as sodium ethoxide, sodium methoxide, sodium hydride, sodium amide, potassium t-butoxide, in a solvent selected, e.g., from the group consisting of methanol, ethanol, tert-butanol, dioxane, DMSO (dimethylsulfoxide) and their mixtures, at a temperature preferably ranging between about 0° C. and 120° C.

The reaction between a compound of formula (IV) and an aldehyde of formula (III) as well as the reaction of a compound of formula (V) with a compound of formula (VI) or with a compound of formula (VII), may, for example, be carried out by treatment with a base such as dimethylsulphinyl carbanion or sodium methoxide or sodium hydride or potassium tert-butoxide, with an alkyllithium or an aryllithium derivative, preferably with methyl-lithium or butyl-lithium or phenyl-lithium, in an organic solvent such as dichloromethane, dichloroethane, benzene, toluene, tetrahydrofuran, dimethylsulfoxide, dimethylformamide, dimethylacetamide or their mixtures at a temperature varying from about 0° C. to about 100° C.

A compound of formula (I) may be converted, as stated above, into another compound of formula (I) by known methods; for example, free hydroxy groups, as substituents in $R_3$ phenyl group, may be etherified by reacting with a suitable alkyl halide in the presence of a base such as $Na_2CO_3$, $K_2CO_3$, NaH, $NaNH_2$, sodium methoxide or sodium ethoxide, in a solvent selected from the group consisting, for example, of methanol, ethanol, dioxane, acetone, dimethylformamide, hexamethylphosphorotriamide, tetrahydrofuran and their mixtures at a temperature ranging preferably between about 0° C. and about 150° C. Furthermore the etherified hydroxy groups may be converted into free hydroxy groups, for example, by treatment with pyridine hydrochloride or with a strong acid such as HCl, HBr or HI, or with a Lewis acid such as $AlCl_3$ or $BBr_3$.

A compound of formula (I) wherein —COR is an esterified carboxy group may be converted into a compound of formula (I) wherein —COR is carboxy by hydrolysis, e.g. basic hydrolysis, using, for example, sodium or potassium hydroxide, in a solvent, such as water or a lower aliphatic alcohol, and operating at a temperature ranging from the room temperature to about 150° C.; the same reaction may be also carried out e.g. by treatment with lithium bromide in dimethylformamide at a temperature higher than 50° C. or by treatment with hydrochloric or hydrobromic or hydroiodic or sulphuric acid in acetic acid at temperatures higher than 50° C.

A compound of formula (I) wherein —COR is carboxy may be converted into a compound of formula (I) wherein —COR is an esterified carboxy group, e.g. a carbalkoxy group unsubstituted or substituted by a pyridyl group or by a

group, wherein $R_4$ and $R_5$ are as defined above, by conventional methods, for example by reacting an alkaline salt of the acid with a suitable alkyl halide in an inert solvent, such as acetone, dioxane, dimethylformamide or hexamethylphosphorotriamide at a temperature ranging from 0° C. to about 100° C.

Alternatively the esterification of a compound of formula (I) wherein —COR is a carboxy group may be effected by converting the carboxylic acid into the corresponding halocarbonyl, preferably chlorocarbonyl, derivative, by reaction, e.g. with the desired acid halide, for example oxalyl chloride, thionyl chloride, $PCl_3$, $PCl_5$ or $POCl_3$, either in the absence of solvents or in an inert organic solvent such as benzene, toluene, xylene, dioxane, dichloroethane, methylene chloride or tetrahydrofuran, at a temperature ranging preferably from about 0° C. to about 120° C.; and then reacting the resulting halocarbonyl derivative with the suitable alcohol of formula R'—OH, wherein R' is $C_1$–$C_6$ alkyl unsubstituted or substituted by a pyridyl group or by a

group, wherein $R_4$ and $R_5$ are as defined above, in an inert solvent such as benzene, toluene, xylene, dioxane, dichloroethane, methylene chloride or tetrahydrofuran, at temperatures varying between about 0° C. and about 120° C., preferably in the presence of a base, such as, triethylamine or pyridine.

Furthermore, for example, a compound of formula (I), wheren —COR is a free carboxy group may be converted into a compound of formula (I) wherein —COR is a

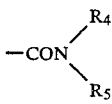

group or a

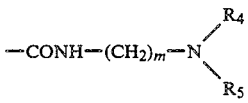

group, wherein m, $R_4$ and $R_5$ are as defined above, by converting, for example, the carboxylic acid into the corresponding halocarbonyl derivative following, e.g., one of the methods described above, and then reacting the halocarbonyl derivative with a compound of formula

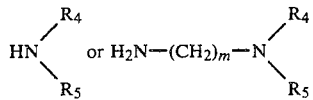

respectively, wherein m, $R_4$ and $R_5$ are as defined above, in an inert solvent such as benzene, toluene, xylene, dioxane, dichloroethane, methylene chloride or tetrahydrofuran, at temperatures varying between about 0° C. and about 120° C., preferably in the presence of a base such as triethylamine or pyridine.

Alternatively, for example, a compound of formula (I) wherein —COR is a —CONH—$(CH_2)_n$—$R_7$ group, wherein n is zero and $R_7$ is as defined above, may be prepared by reacting a compound of formula (I) wherein —COR is a free carboxy group or a $C_2$–$C_7$ carbalkoxy group with a compound of formula $H_2N$—$R_7$, wherein $R_7$ is as defined above, for example, in the presence of polyphosphoric acid at a temperature varying between about 80° C. and about 160° C. in the absence of a solvent or in the presence of an inert organic solvent such as dimethylformamide or dimethylacetamide.

A nitro group as substituent in a phenyl ring in a compound of formula (I) may be converted into an amino group by treatment, for example, with stannous chloride in concentrated hydrochloric acid, using, if necessary, an organic cosolvent such as acetic acid, dioxane, tetrahydrofuran, at a temperature varying between room temperature and about 100° C.

A hydroxy or an amino group as substituents in a phenyl ring in a compound of formula (I) may be converted respectively into a $C_2$–$C_4$ alkanoyloxy or $C_2$–$C_4$ alkanoylamino group using conventional methods well known in organic chemistry.

Also the optional salification of a compound of formula (I) as well as the conversion of a salt into the free compound and the separation of a mixture of isomers into the single isomers may be carried out by conventional methods.

For example the separation of a mixture of optical isomers into the individual isomers may be carried out by salification with an optically active base and subsequent fractional crystallization.

Thus, the separation of a mixture of geometric isomers may be carried out, for example, by fractional crystallization.

The compounds of formula (II) may be prepared, for example, by reacting a compound of formula (VIII)

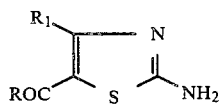

wherein R and $R_1$ are as defined above or a salt thereof, with a compound of formula (IX)

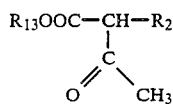 (IX)

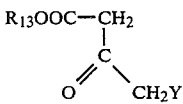 (XII)

wherein $R_2$ is as defined above and $R_{13}$ is hydrogen or $C_1$-$C_6$ alkyl.

Preferred salts of compounds of formula (VIII) are, for example, those with inorganic acid such as hydrochloric, hydrobromic, hydroiodic, phosphoric and sulphuric acid. The reaction between a compound of formula (VIII) or a salt thereof and a compound of formula (IX) may, for example, be carried out in the presence of an acid condensing agent such as polyphosphoric acid (polyphosphoric acid means a mixture of about equal weights of 99% $H_3PO_4$ and $P_2O_5$), sulphuric acid, methanesulphonic acid or p-toluenesulphonic acid, at a temperature ranging preferably between about 50° C. and 150° C.; the reaction may be carried out in an organic solvent such as dimethylformamide, dimethylacetamide, acetic acid, formic acid, benzene, toluene, xylene, ethylene glycol monomethylether or dichloroethane, but it is preferably carried out in the absence of a solvent. The compounds of formula (IV) may be prepared by reacting a compound of formula (X)

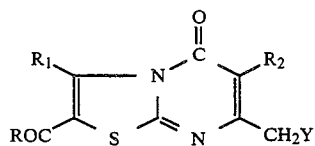 (X)

wherein Y is a radical capable of being converted to an anion $Y^{(-)}$ as defined above, and R, $R_1$ and $R_2$ are as defined above, with $PQ_3$, wherein Q is as defined above, in a solvent such as, benzene, toluene, xylene or acetonitrile at a temperature varying between room temperature and the reflux temperature.

The compounds of formula (V) may be prepared for example by oxidizing a compound of formula (XI)

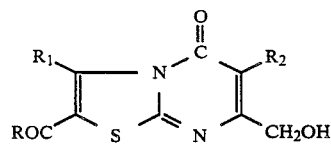 (XI)

wherein R, $R_1$ and $R_2$ are as defined above, for example, with dimethylsulfoxide in the presence of dicyclohexylcarbodiimide and phosphoric acid or pyridinium-trifluoroacetate (Moffat reaction) in a solvent such as benzene, toluene or dimethylsulfoxide at a temperature varying between 0° C. and 50° C.

The compounds of formula (X) wherein $R_2$ is hydrogen may be prepared, for example, by reacting a compound of formula (VIII) or a salt thereof as defined above, with a compound of formula (XII)

wherein $R_{13}$ is as defined above and Y' represents a halogen atom, preferably chlorine or bromine, using the same experimental conditions as for the reaction between a compound of formula (VIII) and a compound of formula (IX). Alternatively the compounds of formula (X) wherein $R_2$ is other than hydrogen, may be prepared, for example, by reacting a compound of formula (II) wherein $R_2$ is other than hydrogen with a N-halosuccinimide, preferably N-bromosuccinimide, in a solvent such as benzene or $CCl_4$ at a temperature varying between room temperature and the reflux temperature.

Alternatively the compounds of formula (X) wherein $R_2$ is chlorine or bromine may be prepared by reacting a compound of formula (X) wherein $R_2$ is hydrogen with a suitable halogenating agent such as chlorosuccinimide or bromosuccinimide, $SO_2Cl_2$ or pyridinium bromide perbromide, operating at a temperature ranging from 0° C. to 100° C. and using, for example, as solvent $CCl_4$ or dichloroethane in the reaction with $SO_2Cl_2$; pyridine in the reaction with pyridinium bromide perbromide and benzene in the reaction with an halosuccinimide.

The compounds of formula (XI) may be prepared, for example, by reacting a compound of formula (X) with potassium or sodium acetate in dimethylformamide at a temperature varying between room temperature and 100° C., so obtaining the corresponding acetoxy-derivative, which in turn is hydrolysed to the corresponding alcohol (XI), for example, by treatment with 37% HCl in dioxane at a temperature varying between room temperature and the reflux temperature. The compounds of formula (III), (VI), (VII), (VIII), (IX) and (XII) are known compounds and may be prepared by conventional methods: in some cases they are commercially available products.

The compounds of formula (I) have antiallergic activity and are therefore useful in the prevention and treatment of all the affections of allergic origin, e.g. bronchial asthma, allergic rhinitis, hay fever, urticaria and dermatosis. The antiallergic activity of the compounds of the invention is shown, e.g., by the fact that they are active in the following biological tests:

in vitro (1) test of A 23187 induced SRS production from rat peritoneal cells, according to M. K. Bach and J. R. Brashler (J. Immunol., 113, 2040, 1974);

(2) test of antigen induced SRS production from guinea-pig chopped lung, according to W. E. Brocklehurst (J. Physiol., 151, 416, 1960);

in vivo (3) test of the IgG mediated passive peritoneal anaphylaxis in the rat, according to H. C. Morse, K. J. Bloch and K. F. Austen (Journal Immunology, 101, 658, (1968); and (4) test of the IgE mediated passive cutaneous anaphylaxis (PCA) in the rat, accorfing to A. M. J. N. Blair (Immunology, 16, 749, 1969).

The results of these biological tests show that the compounds of the invention are active, for example, as inhibitors of the immunological release of allergic mediators, e.g. histamine, from the mast cells and as inhibitors of the production and/or release of anaphylactic mediators such as "slow reacting substances" (SRS) in the peritoneal and the pulmonary system, induced by challenge with an ionophore or with an antigen.

There is evidence that slow reacting substances, recently identified as leukotrienes C, D and E (B. Samuelsson, Prostaglandins, 19, 645, 1980), play an important role in inducing bronchospasm in human allergic asthma (P. Sheard and A. M. J. N. Blair, Int. Arch. Allergy, 38, 217, 1970).

An agent capable of inhibiting the formation of SRS therefore is of therapeutic value in the treatment of allergic asthma.

An important property of the compounds of this invention is that they are active as antiallergic agents also when administered orally.

As preferred example of compound having antiallergic activity the following can be mentioned: 6-chloro-7-trans-(2-phenyl-ethenyl)-5-oxo-5H-thiazolo[3,2-a]pyrimidine-2-carboxylic acid.

In view of their high therapeutic index the compounds of the invention can be safely used in medicine. For example, the approximate acute toxicity ($LD_{50}$) of the compound: 6-chloro-7-trans-(2-phenyl-ethenyl)-5-oxo-5H-thiazolo[3,2-a]pyrimidine-2-carboxylic acid in the mouse, determined with single administration of increasing doses and measured on the seventh day after the day of treatment is per os higher than 800 mg/kg. Analogous toxicity data have been found for the other compounds of the invention.

The compounds of the invention may be administered to humans in conventional manner, for instance orally and parenterally, at a daily dosage preferably of 0.5 to 15 mg/kg, or by inhalation, preferably at a daily dosage of 0.5 to 100 mg, preferably 0.5 to 25 mg, or by topical application, (for example for the treatment of urticaria and dermatosis), e.g. by a cream containing about 0.5–5 mg, preferably 1–2 mg, of the active principle per 100 mg of cream. The nature of the pharmaceutical compositions containing the compounds of this invention in association with pharmaceutically acceptable carriers or diluents will, of course, depend upon the desired route of administration.

The compositions may be formulated in the conventional manner with the usual ingredients. For example, the compounds of the invention may be administered in the form of aqueous or oily solutions or suspensions, aerosols, as well as powders, tablets, pills, gelatine capsules, syrups, drops, suppositories, or creams, or lotions for topical use.

Thus, for oral administration, the pharmaceutical compositions containing the compounds of this invention, are preferably tablets, pills or gelatine capsules which contain the active substance together with diluents, such as, lactose, dextrose, sucrose, mannitol, sorbitol, cellulose; lubricants, for instance, silica, talc, stearic acid, magnesium or calcium stearate, and/or polyethylene glycols; or they may also contain binders, such as, starches, gelatine, methylcellulose, carboxymethylcellulose, gum-arabic, tragacanth, polyvinylpyrrolidone, disaggregrating agents, such as, starches, alginic acid, alginates, sodium starch glycolate; effervescing mixtures; dyestuffs; sweeteners; wetting agents, such as, lecithin, polysorbates, laurylsulphates; and, in general, non-toxic and pharmacologically inactive substances used in pharmaceutical formulations. Said pharmaceutical preparations may be manufactured in known manner, for example, by means of mixing, granulating, tabletting, sugar-coating, or film-coating processes.

For the treatment of allergic asthma, the compounds of the invention are also administered by inhalation. For such use, suitable compositions may comprise a suspension or solution of the active ingredient, preferably in the form of a salt, such as the sodium salt, in water, for administration by means of a conventional nebulizer. Alternatively, the compositions may comprise a suspension or a solution of the active ingredient in a conventional liquified propellant, such as, dichlorodifluoromethane or dichlorotetrafluoroethane to be administered from a pressurized container, i.e., an aerosol dispenser.

When the medicament is not soluble in the propellant, it may be necessary to add a co-solvent, such as, ethanol, dipropylene glycol, isopropyl myristate, and/or surface-active agent to the composition, in order to suspend the medicament in the propellant medium and such surface-active agents may be any of those commonly used for this purpose, such as non-ionic surface-active agents, e.g., lecithin.

The compounds of the invention may also be administered in the form of powders by means of a suitable insufflator device and in this case the fine particle sized powders of the active ingredient may be mixed with a diluent material such a lactose.

Furthermore, the compounds of this invention may also be administered by intradermal or intravenous injection in the conventional manner.

In addition to the internal administration, the compounds of this invention may find use in compositions for topical application, e.g. as creams, lotions or pastes for use in dermatological treatments.

For these compositions the active ingredient may be mixed with conventional oleaginous or emulsifying excipients. The following examples illustrate but do not limit the present invention.

EXAMPLE 1

2-amino-thiazole-5-carboxylic acid, methyl ester (5 g) was reacted with ethyl 2-methyl-acetoacetate (9.11 g) in polyphosphoric acid (25 g: 13.3 g of $H_3PO_4$ and 11.7 g of $P_2O_5$) under stirring at 100° C. for three hours. After cooling, dilution with ice water and neutralization with 20% NaOH, the precipitate was filtered, washed with water and crystallized from $CH_2Cl_2$-hexane to give 6,7-dimethyl-5-oxo-5H-thiazolo[3,2-a]pyrimidine-2-carboxylic acid, methyl ester, m.p. 158°–159° C. (5.46 g), which was reacted with benzaldehyde (3.52 g) in methanol (120 ml) in the presence of sodium methylate (2.7 g) under stirring at reflux temperature for 120 hours. After cooling and concentration in vacuo, the precipitate was filtered and dissolved in a mixture of dimethyl-formamide and formic acid. The solution was diluted with ice water and the precipitate was filtered, washed with water until neutral and crystallized from isopropyl alcohol to give 2.8 g of 6-methyl-7-trans-(2-phenylethenyl)-5-oxo-5H-thiazolo[3,2-a]pyrimidine-2-carboxylic acid, m.p. 257°–259° C., N.M.R. (CF$_3$COOD) δp.p.m.: 2.50 (s) (3H, —CH$_3$), 7.36 (d) (1H, β-ethenyl proton), 7.40–7.90 (m) (5H, phenyl protons), 7.73 (d) (1H, α-ethenyl proton), 9.07 (s) (1H, C-3 proton), $J_{H\alpha H\beta}=16$ Hz.

By proceeding analogously, using the suitable ethyl acetoacetates, the following compounds were prepared:

7-trans-(2-phenyl-ethenyl)-5-oxo-5H-thiazolo[3,2-a]pyrimidine-2-carboxylic acid, m.p. 246°–248° C.;

6-ethyl-7-trans-(2-phenyl-ethenyl)-5-oxo-5H-thiazolo[3,2-a]pyrimidine-2-carboxylic acid, m.p. 254°–256° C.;

6-propyl-7-trans-(2-phenyl-ethenyl)-5-oxo-5H-thiazolo[3,2-a]pyrimidine-2-carboxylic acid, m.p. 255°–257° C.; and 6-chloro-7-trans-(2-phenyl-ethenyl)-5-oxo-5H-thiazolo[3,2-a]pyrimidine-2-carboxylic acid, m.p. 265°–270° dec.

EXAMPLE 2

6,7-dimethyl-5-oxo-5H-thiazolo[3,2-a]pyrimidine-2-carboxylic acid, methyl ester (2 g), prepared according to Example 1, was reacted with 2 methyl-benzaldehyde (2.02 g) in methanol (60 ml) in the presence of sodium methoxide (1.36 g) under stirring at the reflux temperature for 48 hours. After cooling the precipitate was filtered and dissolved in a mixture of dimethyl-formamide and formic acid: the solution was diluted with ice water and the precipitate was filtered and washed with water until neutral. Crystallization from methanol gave 0.67 g of 6-methyl-7-trans-[2-(2-methyl-phenyl)-ethenyl]-5-oxo-5H-thiazolo[3,2-a]pyrimidine-2-carboxylic acid, m.p. 251°–254° C. N.M.R. (CDCl$_3$+CF$_3$COOD) δp.p.m.: 2.44 (s) (6H, —CH$_3$), 7.15 (d) (1H, β-ethenyl proton), 7.34 (m) (3H, C-3, C-4 and C-5 phenyl protons), 7.68 (m) (1H, C-6 phenyl proton), 7.96 (d) (1H, α-ethenyl proton), 8.93 (s) (1H, C-3 proton); $J_{H\alpha,H\beta}=16$ Hz.

By proceeding analogously, using the suitable aldehydes, the following compounds were prepared:

6-methyl-7-trans-[2-(3-methyl-phenyl)-ethenyl]-5-oxo-5H-thiazolo[3,2-a]pyrimidine-2-carboxylic acid, m.p. 241°–244° C.;

6-methyl-7-trans-[2-(4-methyl-phenyl)-ethenyl]-5-oxo-5H-thiazolo[3,2-a]pyrimidine-2-carboxylic acid, m.p. 252°–255° C.;

6-methyl-7-trans-[2-(2,4-dimethyl-phenyl)-ethenyl]-5-oxo-5H-thiazolo[3,2-a]pyrimidine-2-carboxylic acid, m.p. 272°–275° C.;

6-methyl-7-trans-[2-(2,5-dimethyl-phenyl)-ethenyl]-5-oxo-5H-thiazolo[3,2-a]pyrimidine-2-carboxylic acid, m.p. 257°–260° C.;

6-methyl-7-trans-[2-(2-methoxy-phenyl)-ethenyl]-5-oxo-5H-thiazolo[3,2-a]pyrimidine-2-carboxylic acid, m.p. 241°–244° C.;

6-methyl-7-trans-[2-(3-methoxy-phenyl)-ethenyl]-5-oxo-5H-thiazolo[3,2-a]pyrimidine-2-carboxylic acid, m.p. 255°–258° C.;

6-methyl-7-trans-[2-(4-methoxy-phenyl)-ethenyl]-5-oxo-5H-thiazolo[3,2-a]pyrimidine-2-carboxylic acid, m.p. 255°–257° C.;

6-methyl-7-trans-[2-(2-ethoxy-phenyl)-ethenyl]-5-oxo-5H-thiazolo[3,2-a]pyrimidine-2-carboxylic acid;

6-methyl-7-trans-[2-(3-ethoxy-phenyl)-ethenyl]-5-oxo-5H-thiazolo[3,2-a]pyrimidine-2-carboxylic acid;

6-methyl-7-trans-[2-(2,3-dimethoxy-phenyl)-ethenyl]-5-oxo-5H-thiazolo[3,2-a]pyrimidine-2-carboxylic acid, m.p. 254°–256° C.;

6-methyl-7-trans-[2-(2-methoxy-3-ethoxy-phenyl)-ethenyl]-5-oxo-5H-thiazolo[3,2-a]pyrimidine-2-carboxylic acid, m.p. 242°–244° C.;

6-methyl-7-trans-[2-(2-ethoxy-3-methoxy-phenyl)-ethenyl]-5-oxo-5H-thiazolo[3,2-a]pyrimidine-2-carboxylic acid;

6-methyl-7-trans-[2-(2,5-dimethoxy-phenyl)-ethenyl]-5-oxo-5H-thiazolo[3,2-a]pyrimidine-2-carboxylic acid, m.p. 245°–247° C.;

6-methyl-7-trans-[2-(3,4-dimethoxy-phenyl)-ethenyl]-5-oxo-5H-thiazolo[3,2-a]pyrimidine-2-carboxylic acid;

6-methyl-7-trans-[2-(2,4-dimethoxy-phenyl)-ethenyl]-5-oxo-5H-thiazolo[3,2-a]pyrimidine-2-carboxylic acid;

6-methyl-7-trans-[2-(3,5-dimethoxy-phenyl)-ethenyl]-5-oxo-5H-thiazolo[3,2-a]pyrimidine-2-carboxylic acid;

6-methyl-7-trans-[2-(3-chloro-phenyl)-ethenyl]-5-oxo-5H-thiazolo[3,2-a]pyrimidine-2-carboxylic acid;

6-methyl-7-trans-[2-(3,4,5-trimethoxy-phenyl)-ethenyl]-5-oxo-5H-thiazolo[3,2-a]pyrimidine-2-carboxylic acid;

6-methyl-7-trans-[2-(4-chloro-phenyl)-ethenyl]-5-oxo-5H-thiazolo[3,2-a]pyrimidine-2-carboxylic acid, m.p. 281°–284° C.;

6-methyl-7-trans-[2-(2-fluoro-phenyl)-ethenyl]-5-oxo-5H-thiazolo[3,2-a]pyrimidine-2-carboxylic acid;

6-methyl-7-trans-[2-(3-fluoro-phenyl)-ethenyl]-5-oxo-5H-thiazolo[3,2-a]pyrimidine-2-carboxylic acid;

6-methyl-7-trans-[2-(2-chloro-phenyl)-ethenyl]-5-oxo-5H-thiazolo[3,2-a]pyrimidine-2-carboxylic acid;

6-methyl-7-trans-[2-(2,6-dichloro-phenyl)-ethenyl]-5-oxo-5H-thiazolo[3,2-a]pyrimidine-2-carboxylic acid, m.p. 265°–268° C.;

6-methyl-7-trans-[2-(3,4-dichloro-phenyl)-ethenyl]-5-oxo-5H-thiazolo[3,2-a]pyrimidine-2-carboxylic acid;

6-methyl-7-trans-[2-(4-fluoro-phenyl)-ethenyl]-5-oxo-5H-thiazolo[3,2-a]pyrimidine-2-carboxylic acid, m.p. 230°–234° C.;

6-methyl-7-trans-[2-(4-ethoxy-phenyl)-ethenyl]-5-oxo-5H-thiazolo[3,2-a]pyrimidine-2-carboxylic acid;

6-methyl-7-trans-[2-(2-nitro-phenyl)-ethenyl]-5-oxo-5H-thiazolo[3,2-a]pyrimidine-2-carboxylic acid;

6-methyl-7-trans-[2-(3-nitro-phenyl)-ethenyl]-5-oxo-5H-thiazolo[3,2-a]pyrimidine-2-carboxylic acid;

6-methyl-7-trans-[2-(4-nitro-phenyl)-ethenyl]-5-oxo-5H-thiazolo[3,2-a]pyrimidine-2-carboxylic acid;

6-methyl-7-trans-[2-(4-amino-phenyl)-ethenyl]-5-oxo-5H-thiazolo[3,2-a]pyrimidine-2-carboxylic acid;

6-methyl-7-trans-[2-(2,3,4-trimethoxy-phenyl)-ethenyl]-5-oxo-5H-thiazolo[3,2-a]pyrimidine-2-carboxylic acid; and 6-methyl-7-trans-[2-(2,4-dichloro-phenyl)-ethenyl]-5-oxo-5H-thiazolo[3,2-a]pyrimidine-2-carboxylic acid.

EXAMPLE 3

6,7-dimethyl-5-oxo-5H-thiazolo[3,2-a]pyrimidine-2-carboxylic acid, methyl ester (3.5 g), prepared according to Example 1, was reacted with 2-pyridinecarboxaldehyde (5.5 g) in methanol (100 ml) in the presence of sodium methoxide (2.75 g) under stirring at the reflux temperature for 42 hours. After cooling the precipitate was filtered and dissolved in formic acid: the solution was diluted with ice water and the precipitate was filtered and washed with water until neutral. Crystallization from methanol gave 2.4 g of 6-methyl-7-trans-[2-(2-pyridyl)-ethenyl]-5-oxo-5H-thiazolo[3,2-a]pyrimidine-2-carboxylic acid, m.p. 260°–265° C., N.M.R. (CDCl$_3$—CF$_3$COOD) δp.p.m.: 2.45 (s) (3H, CH$_3$), 8.02 (d) and 8.06 (d) (2H, ethenyl protons), 8.02 (dd) (1H, C-5 pyridyl proton), 8.38 (bd) (1H, C-3 pyridyl proton), 8.60 (bd) (1H, C-4 pyridyl proton), 8.78 (d) (1H, C-6 pyridyl proton), 8.84 (s) (1H, C-3 proton); J$_{HαHβ}$=16 Hz.

By proceeding analogously using suitable heteroaryl aldehydes, the following compounds were prepared:
6-methyl-7-trans-[2-(3-pyridyl)-ethenyl]-5-oxo-5H-thiazolo[3,2-a]pyrimidine-2-carboxylic acid, m.p. 272°–275° C.;
6-methyl-7-trans-[2-(4-pyridyl)-ethenyl]-5-oxo-5H-thiazolo[3,2-a]pyrimidine-2-carboxylic acid; and
6-methyl-7-trans-[2-(2-thienyl)-ethenyl]-5-oxo-5H-thiazolo[3,2-a]pyrimidine-2-carboxylic acid.

EXAMPLE 4

By proceeding according to Example 1, 2 and 3, using suitable acetoacetates and aldehydes, the following compounds were prepared:
7-trans-[2-(2-methyl-phenyl)-ethenyl]-5-oxo-5H-thiazolo[3,2-a]pyrimidine-2-carboxylic acid;
7-trans-[2-(3-methyl-phenyl)-ethenyl]-5-oxo-5H-thiazolo[3,2-a]pyrimidine-2-carboxylic acid;
7-trans-[2-(4-methoxy-phenyl)-ethenyl]-5-oxo-5H-thiazolo[3,2-a]pyrimidine-2-carboxylic acid;
7-trans-[2-(4-methyl-phenyl)-ethenyl]-5-oxo-5H-thiazolo[3,2-a]pyrimidine-2-carboxylic acid;
7-trans-[2-(2,3-dimethoxy-phenyl)-ethenyl]-5-oxo-5H-thiazolo[3,2-a]pyrimidine-2-carboxylic acid;
7-trans-[2-(4-ethoxy-phenyl)-ethenyl]-5-oxo-5H-thiazolo[3,2-a]pyrimidine-2-carboxylic acid;
7-trans-[2-(2,5-dimethyl-phenyl)-ethenyl]-5-oxo-5H-thiazolo[3,2-a]pyrimidine-2-carboxylic acid;
6-ethyl-7-trans-[2-(2-methyl-phenyl)-ethenyl]-5-oxo-5H-thiazolo[3,2-a]pyrimidine-2-carboxylic acid;
6-ethyl-7-trans-[2-(3-methyl-phenyl)-ethenyl]-5-oxo-5H-thiazolo[3,2-a]pyrimidine-2-carboxylic acid;
6-ethyl-7-trans-[2-(4-methoxy-phenyl)-ethenyl]-5-oxo-5H-thiazolo[3,2-a]pyrimidine-2-carboxylic acid;
6-ethyl-7-trans-[2-(4-methyl-phenyl)-ethenyl]-5-oxo-5H-thiazolo[3,2-a]pyrimidine-2-carboxylic acid;
6-ethyl-7-trans-[2-(2,3-dimethoxy-phenyl)-ethenyl]-5-oxo-5H-thiazolo[3,2-a]pyrimidine-2-carboxylic acid;
6-ethyl-7-trans-[2-(4-ethoxy-phenyl)-ethenyl]-5-oxo-5H-thiazolo[3,2-a]pyrimidine-2-carboxylic acid;
6-ethyl-7-trans-[2-(2,5-dimethyl-phenyl)-ethenyl]-5-oxo-5H-thiazolo[3,2-a]pyrimidine-2-carboxylic acid;
6-ethyl-7-trans-[2-(3-pyridyl)-ethenyl]-5-oxo-5H-thiazolo[3,2-a]pyrimidine-2-carboxylic acid; and
6-ethyl-7-trans-[2-(2-thienyl)-ethenyl]-5-oxo-5H-thiazolo[3,2-a]pyrimidine-2-carboxylic acid.

EXAMPLE 5

7-methyl-5-oxo-5H-thiazolo[3,2-a]pyrimidine-2-carboxylic acid, methyl ester (5.5 g; m.p. 146°–148° C.), prepared according to Example 1, was reacted with sulfuryl chloride (3.6 g) in dichloroethane (150 ml) under stirring at room temperature for 30 minutes. The reaction mixture was poured into ice water containing NaHCO$_3$: the organic phase was separated and evaporated in vacuo to dryness: crystallization from methanol gave 6-chloro-7-methyl-5-oxo-5H-thiazolo[3,2-a]pyrimidine-2-carboxylic acid, methyl ester (4.28 g), m.p. 218°–220° C., which was reacted with benzaldehyde (3.5 g) in methanol (150 ml) in the presence of sodium methoxide (2.68 g) under stirring at reflux temperature for 24 hours. The precipitate was filtered and dissolved in a mixture of dimethylformamide and formic acid; the solution was diluted with ice water and the precipitate was filtered and washed with water until neutral. Crystallization from CH$_2$Cl$_2$-methanol gave 3.1 g of 6-chloro-7-trans-(2-phenyl-ethenyl)-5-oxo-5H-thiazolo[3,2-a]pyrimidine-2-carboxylic acid, m.p. 265°–270° C. dec., N.M.R. (CF$_3$COOD-CDCl$_3$) δp.p.m.: 7.59 (d) (1H,β-ethenyl proton), 7.40–7.80 (m) (5H, phenyl protons), 8.01 (d) (1H,α-ethenyl proton), 8.88 (s) (1H, C-3 proton); J$_{HαHβ}$=16 Hz.

By proceeding analogously, using suitable aldehydes, the following compounds were prepared:
6-chloro-7-trans-[2-(2-methyl-phenyl)-ethenyl]-5-oxo-5H-thiazolo[3,2-a]pyrimidine-2-carboxylic acid, m.p. 270°–273° C.;
6-chloro-7-trans-[2-(3-methyl-phenyl)-ethenyl]-5-oxo-5H-thiazolo[3,2-a]pyrimidine-2-carboxylic acid, m.p. 270°–272° C.;
6-chloro-7-trans-[2-(4-methyl-phenyl)-ethenyl]-5-oxo-5H-thiazolo[3,2-a]pyrimidine-2-carboxylic acid, m.p. 280°–285° C.;
6-chloro-7-trans-[2-(2-methoxy-phenyl)-ethenyl]-5-oxo-5H-thiazolo[3,2-a]pyrimidine-2-carboxylic acid, m.p. 262°–266° C.;
6-chloro-7-trans-[2-(3-methoxy-phenyl)-ethenyl]-5-oxo-5H-thiazolo[3,2-a]pyrimidine-2-carboxylic acid, m.p. 262°–267° C.;
6-chloro-7-trans-[2-(4-methoxy-phenyl)-ethenyl]-5-oxo-5H-thiazolo[3,2-a]pyrimidine-2-carboxylic acid, m.p. 269°–274° C.;
6-chloro-7-trans-[2-(2,3-dimethoxy-phenyl)-ethenyl]-5-oxo-5H-thiazolo[3,2-a]pyrimidine-2-carboxylic acid, m.p. 263°–265° C.;
6-chloro-7-trans-[2-(2,5-dimethoxy-phenyl)-ethenyl]-5-oxo-5H-thiazolo[3,2-a]pyrimidine-2-carboxylic acid, m.p. 271°–273° C.;
6-chloro-7-trans-[2-(3-ethoxy-phenyl)-ethenyl]-5-oxo-5H-thiazolo[3,2-a]pyrimidine-2-carboxylic acid;
6-chloro-7-trans-[2-(4-fluoro-phenyl)-ethenyl]-5-oxo-5H-thiazolo[3,2-a]pyrimidine-2-carboxylic acid, m.p. 283°–288° C. dec.;
6-chloro-7-trans-[2-(4-chloro-phenyl)-ethenyl]-5-oxo-5H-thiazolo[3,2-a]pyrimidine-2-carboxylic acid, m.p. 305°–307° C.;
6-chloro-7-trans-[2-(3-pyridyl)-ethenyl]-5-oxo-5H-thiazolo[3,2-a]pyrimidine-2-carboxylic acid, m.p. 235°–240° C. dec.;

6-chloro-7-trans-[2-(4-pyridyl)-ethenyl]-5-oxo-5H-thiazolo[3,2-a]pyrimidine-2-carboxylic acid;
6-chloro-7-trans-[2-(2-thienyl)-ethenyl]-5-oxo-5H-thiazolo[3,2-a]pyrimidine-2-carboxylic acid, m.p. 284°–286° C.;
6-chloro-7-trans-[2-(2-methoxy-3-ethoxy-phenyl)-ethenyl]-5-oxo-5H-thiazolo[3,2-a]pyrimidine-2-carboxylic acid, m.p. 255°–257° C.;
6-chloro-7-trans-[2-(2-pyridyl)-ethenyl]-5-oxo-5H-thiazolo[3,2-a]pyrimidine-2-carboxylic acid;
6-chloro-7-trans-[2-(2-chloro-phenyl)-ethenyl]-5-oxo-5H-thiazolo[3,2-a]pyrimidine-2-carboxylic acid, m.p. 277°–280° C.;
6-chloro-7-trans-[2-(3-chloro-phenyl)-ethenyl]-5-oxo-5H-thiazolo[3,2-a]pyrimidine-2-carboxylic acid, m.p. 276°–278° C.;
6-chloro-7-trans-[2-(2-fluoro-phenyl)-ethenyl]-5-oxo-5H-thiazolo[3,2-a]pyrimidine-2-carboxylic acid;
6-chloro-7-trans-[2-(3-fluoro-phenyl)-ethenyl]-5-oxo-5H-thiazolo[3,2-a]pyrimidine-2-carboxylic acid;
6-chloro-7-trans-[2-(2,4-dimethyl-phenyl)-ethenyl]-5-oxo-5H-thiazolo[3,2-a]pyrimidine-2-carboxylic acid;
6-chloro-7-trans-[2-(2,5-dimethyl-phenyl)-ethenyl]-5-oxo-5H-thiazolo[3,2-a]pyrimidine-2-carboxylic acid, m.p. 276°–279° C.;
6-chloro-7-trans-[2-(2-ethoxy-phenyl)-ethenyl]-5-oxo-5H-thiazolo[3,2-a]pyrimidine-2-carboxylic acid, m.p. 276°–278° C.;
6-chloro-7-trans-[2-(4-ethoxy-phenyl)-ethenyl]-5-oxo-5H-thiazolo[3,2-a]pyrimidine-2-carboxylic acid, m.p. 270°–272° C.;
6-chloro-7-trans-[2-(3,4-dimethoxy-phenyl)-ethenyl]-5-oxo-5H-thiazolo[3,2-a]pyrimidine-2-carboxylic acid;
6-chloro-7-trans-[2-(2,4-dimethoxy-phenyl)-ethenyl]-5-oxo-5H-thiazolo[3,2-a]pyrimidine-2-carboxylic acid;
6-chloro-7-trans-[2-(3,5-dimethoxy-phenyl)-ethenyl]-5-oxo-5H-thiazolo[3,2-a]pyrimidine-2-carboxylic acid;
6-chloro-7-trans-[2-(2-nitro-phenyl)-ethenyl]-5-oxo-5H-thiazolo[3,2-a]pyrimidine-2-carboxylic acid;
6-chloro-7-trans-[2-(3-nitro-phenyl)-ethenyl]-5-oxo-5H-thiazolo[3,2-a]pyrimidine-2-carboxylic acid;
6-chloro-7-trans-[2-(4-nitro-phenyl)-ethenyl]-5-oxo-5H-thiazolo[3,2-a]pyrimidine-2-carboxylic acid, m.p. 245°–260° C. dec.;
6-chloro-7-trans-[2-(2-ethoxy-3-methoxy-phenyl)-ethenyl]-5-oxo-5H-thiazolo[3,2-a]pyrimidine-2-carboxylic acid;
6-chloro-7-trans-[2-(2,3,4-trimethoxy-phenyl)-ethenyl]-5-oxo-5H-thiazolo[3,2-a]pyrimidine-2-carboxylic acid;
6-chloro-7-trans-[2-(3,4,5-trimethoxy-phenyl)-ethenyl]-5-oxo-5H-thiazolo[3,2-a]pyrimidine-2-carboxylic acid, m.p. 270°–272° C.;
6-chloro-7-trans-[2-(2,4,5-trimethoxy-phenyl)-ethenyl]-5-oxo-5H-thiazolo[3,2-a]pyrimidine-2-carboxylic acid;
6-chloro-7-trans-[2-(4-hydroxy-phenyl)-ethenyl]-5-oxo-5H-thiazolo[3,2-a]pyrimidine-2-carboxylic acid;
6-chloro-7-trans-[2-(4-amino-phenyl)-ethenyl]-5-oxo-5H-thiazolo[3,2-a]pyrimidine-2-carboxylic acid,
6-chloro-7-trans-[2-(2,6-dichloro-phenyl)-ethenyl]-5-oxo-5H-thiazolo[3,2-a]pyrimidine-2-carboxylic acid, m.p. 290°–293° C.;
6-chloro-7-trans-[2-(2,4-dichloro-phenyl)-ethenyl]-5-oxo-5H-thiazolo[3,2-a]pyrimidine-2-carboxylic acid; and
6-chloro-7-trans-[2-(3,4-dichloro-phenyl)-ethenyl]-5-oxo-5H-thiazolo[3,2-a]pyrimidine-2-carboxylic acid.

EXAMPLE 6

7-methyl-5-oxo-5H-thiazolo[3,2-a]pyrimidine-2-carboxylic acid, methyl ester (3.4 g), prepared according to Example 1, was reacted with pyridinium bromide perbromide (5.31 g) in anhydrous pyridine (80 ml) under stirring at room temperature for 40 minutes. The reaction mixture was poured in ice water and the precipitate was filtered and washed with water until neutral. The crude compound was purified over a $SiO_2$ column, using chloroform:ethyl acetate 100:5 as eluent, so obtaining 3.3 g of 6-bromo-7-methyl-5-oxo-5H-thiazolo[3,2-a]pyrimidine-2-carboxylic acid, methyl ester, m.p. 199°–201° C., which was reacted with benzaldehyde (2.3 g) in methanol (90 ml) in the presence of sodium methoxide (0.75 g) under stirring at reflux temperature for 48 hours. The precipitate was filtered and dissolved in a mixture of dimethylformamide and formic acid: the solution was diluted with ice water and the precipitate was filtered and washed with water until neutral. Crystallization from methanol gave 2.4 g of 6-bromo-7-trans-(2-phenyl-ethenyl)-5-oxo-5H-thiazolo[3,2-a]pyrimidine-2-carboxylic acid, m.p. 281°–285° C.

By proceeding analogously the following compounds were prepared:
6-bromo-7-trans-[2-(3-methyl-phenyl)-ethenyl]-5-oxo-5H-thiazolo[3,2-a]pyrimidine-2-carboxylic acid;
6-bromo-7-trans-[2-(2,5-dimethyl-phenyl)-ethenyl]-5-oxo-5H-thiazolo[3,2-a]pyrimidine-2-carboxylic acid;
6-bromo-7-trans-[2-(4-methyl-phenyl)-ethenyl]-5-oxo-5H-thiazolo[3,2-a]pyrimidine-2-carboxylic acid; and
6-bromo-7-trans-[2-(2-methyl-phenyl)-ethenyl]-5-oxo-5H-thiazolo[3,2-a]pyrimidine-2-carboxylic acid.

EXAMPLE 7

2-amino-thiazole-5-carboxylic acid, methyl ester (5 g) was reacted with ethyl 4-chloro-acetoacetate (10.6 g) in polyphosphoric acid (25 g) under stirring at 100° C. for 4 hours. After cooling, dilution with ice water and neutralization with 35% NaOH, the precipitate was extracted with ethyl acetate and purified over a $SiO_2$ column using n-hexane/ethyl acetate as eluent. Crystallization from isopropyl ether gave 7-chloromethyl-5-oxo-5H-thiazolo[3,2-a]pyrimidine-2-carboxylic acid, methyl ester, m.p. 139°–141° C. (2.75 g) which was reacted with triphenylphosphine (3.15 g) in acetonitrile (100 ml) under stirring at reflux temperature for 16 hours. After cooling the precipitate was filtered and washed with acetonitrile to give (2-carbomethoxy-5-oxo-5H-thiazolo[3,2-a]pyrimidine-7-yl)-methyl-triphenyl-phosphonium chloride, m.p. 180°–181° C. dec. (3.35 g) which was added under stirring to a suspension of 75% NaH (0.3 g) in dimethylsulphoxide (60 ml) and dichloroethane (40 ml) and reacted with 3-pyridine carboxaldehyde (1.4 g) at room temperature for 20 hours. The solution was then diluted with ice water and the crude precipitate was extracted with dichloroethane: the organic phase was separated and evaporated in vacuo to dryness. The crude residue was crystallized from isopropyl alcohol to give 7-trans-[2-(3-pyridyl)-ethenyl]-5-oxo-5H-thiazolo[3,2-a]pyrimidine-2-carboxylic acid, methyl ester (1.3 g) which was hydrolyzed by treatment with a mixture 37% HCl:acetic acid = 1:1 (50 ml) at the reflux temperature for 40 hours. After cooling the reaction mixture was diluted with ice water and neutralized with 37% NaOH: the precipitate was filtered and washed with water until neutral. Crystallization from CHCl$_3$-ethanol gave 0.87 g of 7-trans-[2-(3-pyridyl)-ethenyl]-5-oxo-5H-thiazolo[3,2-a]pyrimidine-2-carboxylic acid, m.p. 264°–267° C., N.M.R. (CDCl$_3$-CF$_3$COOD) δp.p.m.: 6.95 (s) (1H, C-6 proton), 7.53 (d) (1H,β-ethenyl proton), 8.02 (d) (1H,α-ethenyl proton), 8.20 (dd) (1H, C-5 pyridyl proton), 8.60–9.03 (m) (2H, C-4 and C-6 pyridyl protons), 8.90 (s) (1H, C-3 proton), 9.11 (bs) (1H, C-2 pyridyl proton), $J_{H\alpha H\beta}$ = 16 Hz.

By proceeding analogously the following compounds were prepared:
7-trans-[2-(2-pyridyl)-ethenyl]-5-oxo-5H-thiazolo[3,-2,a]pyrimidine-2-carboxylic acid;
7-trans-[2-(6-methyl-2-pyridyl)-ethenyl]-5-oxo-5H-thiazolo[3,2-a]pyrimidine-2-carboxylic acid;
7-trans-[2-(2-thienyl)-ethenyl]-5-oxo-5H-thiazolo[3,2-a]pyrimidine-2-carboxylic acid;
3-methyl-7-trans-[2-(2-methyl-phenyl)-ethenyl]-5-oxo-5H-thiazolo[3,2-a]pyrimidine-2-carboxylic acid;
3-methyl-7-trans-[2-(3-methyl-phenyl)-ethenyl]-5-oxo-5H-thiazolo[3,2-a]pyrimidine-2-carboxylic acid;
3-phenyl-7-trans-[2-(2-methyl-phenyl)-ethenyl]-5-oxo-5H-thiazolo[3,2-a]pyrimidine-2-carboxylic acid; and
3-phenyl-7-trans-[2-(3-methyl-phenyl)-ethenyl]-5-oxo-5H-thiazolo[3,2-a]pyrimidine-2-carboxylic acid.

EXAMPLE 8

2-amino-4-methyl-thiazole-5-carboxylic acid, ethyl ester (10 g) was reacted with ethyl 2-ethyl-acetoacetate (17 g) in polyphosphoric acid (50 g) under stirring at 100° C. for 4 hours. After cooling, dilution with ice water and neutralization with 35% NaOH, the precipitate was filtered, washed with water until neutral and crystallized from hexane to give 6-ethyl-3,7-dimethyl-5-oxo-5H-thiazolo[3,2-a]pyrimidine-2-carboxylic acid, ethyl ester, m.p. 122°–124° C. (9.9 g) which was reacted with N-bromo succinimide (13.75 g) in benzene (260 ml) at the reflux temperature for 11 hours.

After cooling the solution was diluted with ethyl acetate and shaken with 5% NaHCO$_3$ and then with water until neutral. Evaporation in vacuo to dryness and crystallization of the residue from isopropyl ether gave 7-bromomethyl-6-ethyl-3-methyl-5-oxo-5H-thiazolo[3,2-a]pyrimidine-2-carboxylic acid, ethyl ester, m.p. 146°–148° C. (6.7 g) which was reacted with triphenyl phosphine (5.4 g) in benzene (160 ml) under stirring at reflux temperature for 5 hours.

After cooling the precipitate was filtered and washed with benzene to give (2-carbethoxy-6-ethyl-3-methyl-5-oxo-5H-thiazolo[3,2-a]pyrimidine-7-yl)-methyl-triphenylphosphonium bromide, m.p. 152° C. (9.7 g) which was dissolved in dichloroethane (80 ml) and treated dropwise with a 1.6M hexane solution of n-butyl-lithium (10.6 ml) at −15° C. A solution of benzaldehyde (2.47 g) in dichloroethane (10 ml) was added dropwise under stirring maintaining the temperature at −15° C.: the reaction mixture was stirred first for 3 hours at −10° C. then for 5 hours at room temperature. The reaction mixture was finally neutralized with NaH$_2$PO$_4$ and diluted with ice water then was extracted with ethyl acetate. The organic layer was separated and evaporated to dryness: crystallization of the residue from CH$_2$Cl$_2$-methanol gave 6-ethyl-3-methyl-7-trans-(2-phenyl-ethenyl)-5-oxo-5H-thiazolo[3,2-a]pyrimidine-2-carboxylic acid, ethyl ester, m.p. 175°–176° C. (4 g) which was hydrolyzed by treatment with 1% KOH in methanol solution (67 ml) at reflux temperature for 30 minutes. After cooling the precipitated potassium salt was recovered by filtration, then dissolved in hot formic acid. Dilution with ice water gave a precipitate which was filtered and washed with water until neutral: washings with chloroform gave pure 6-ethyl-3-methyl-7-trans-(2-phenyl-ethenyl)-5-oxo-5H-thiazolo[3,2-a]pyrimidine-2-carboxylic acid (3.1 g) m.p. 257°–260° C.

By proceeding analogously the following compounds were prepared:
6-ethyl-3-methyl-7-trans-[2-(2-methyl-phenyl)-ethenyl]-5-oxo-5H-thiazolo[3,2-a]pyrimidine-2-carboxylic acid;
6-ethyl-3-methyl-7-trans-[2-(3-methyl-phenyl)-ethenyl]-5-oxo-5H-thiazolo[3,2-a]pyrimidine-2-carboxylic acid;
6-ethyl-3-phenyl-7-trans-[2-(2-methyl-phenyl)-ethenyl]-5-oxo-5H-thiazolo[3,2-a]pyrimidine-2-carboxylic acid; and
6-ethyl-3-phenyl-7-trans-[2-(3-methyl-phenyl)-ethenyl]-5-oxo-5H-thiazolo[3,2-a]pyrimidine-2-carboxylic acid.

EXAMPLE 9

2-amino-4-methyl-thiazole-5-carboxylic acid, ethyl ester (1.5 g) was reacted with ethyl 2-chloro-acetoacetate (2.65 g) in polyphosphoric acid (20 g) under stirring at 100° C. for 3 hours.

After cooling, dilution with ice water and neutralization with 30% NaOH, the precipitate was extracted with ethyl acetate and the organic solution was evaporated in vacuo to dryness. The residue was purified over a SiO$_2$ column using hexane-ethyl acetate 70:30 as eluent:crystallization from hexane gave 6-chloro-3,7-dimethyl-5-oxo-5H-thiazolo[3,2-a]pyrimidine-2-carboxylic acid, methyl ester, m.p. 140°–141° C. (1.52 g), which was reacted with benzaldehyde (1.2 g) in tert-butanol (30 ml) in the presence of potassium tert-butylate (1.8 g) under stirring at 25° C. for 3 hours.

Then the reaction mixture was diluted with ice water containing excess NaH$_2$PO$_4$ and the precipitate was extracted with chloroform: the organic solution was evaporated in vacuo to dryness. Crystallization from methanol gave 0.6 g of 6-chloro-3-methyl-7-trans-(2-phenyl-ethenyl)-5-oxo-5H-thiazolo[3,2-a]pyrimidine-2-carboxylic acid, m.p. 248°–250° C.

By proceeding analogously, the following compounds were prepared
3,6-dimethyl-7-trans-[2-(2-methyl-phenyl)-ethenyl]-5-oxo-5H-thiazolo[3,2-a]pyrimidine-2-carboxylic acid;
3,6-dimethyl-7-trans-[2-(3-methyl-phenyl)-ethenyl]-5-oxo-5H-thiazolo[3,2-a]pyrimidine-2-carboxylic acid;
3,6-dimethyl-7-trans-[2-(3-ethoxy-phenyl)-ethenyl]-5-oxo-5H-thiazolo[3,2-a]pyrimidine-2-carboxylic acid;
3,6-dimethyl-7-trans-[2-(4-methyl-phenyl)-ethenyl]-5-oxo-5H-thiazolo[3,2-a]pyrimidine-2-carboxylic acid;

3,6-dimethyl-7-trans-(2-phenyl-ethenyl)-5-oxo-5H-thiazolo[3,2-a]pyrimidine-2-carboxylic acid;

6-chloro-3-methyl-7-trans-[2-(2-methyl-phenyl)-ethenyl]-5-oxo-5H-thiazolo[3,2-a]pyrimidine-2-carboxylic acid;

6-chloro-3-methyl-7-trans-[2-(3-methyl-phenyl)-ethenyl]-5-oxo-5H-thiazolo[3,2-a]pyrimidine-2-carboxylic acid;

6-chloro-3-methyl-7-trans-[2-(4-fluoro-phenyl)-ethenyl]-5-oxo-5H-thiazolo[3,2-a]pyrimidine-2-carboxylic acid;

6-chloro-3-methyl-7-trans-[2-(4-methyl-phenyl)-ethenyl]-5-oxo-5H-thiazolo[3,2-a]pyrimidine-2-carboxylic acid;

6-chloro-3-phenyl-7-trans-[2-(4-fluoro-phenyl)-ethenyl]-5-oxo-5H-thiazolo[3,2-a]pyrimidine-2-carboxylic acid;

3,6-dimethyl-7-trans-[2-(2,5-dimethyl-phenyl)-ethenyl]-5-oxo-5H-thiazolo[3,2-a]pyrimidine-2-carboxylic acid;

6-chloro-3-methyl-7-trans-[2-(2,5-dimethyl-phenyl)-ethenyl]-5-oxo-5H-thiazolo[3,2-a]pyrimidine-2-carboxylic acid;

6-methyl-3-phenyl-7-trans-[2-(2-methyl-phenyl)-ethenyl]-5-oxo-5H-thiazolo[3,2-a]pyrimidine-2-carboxylic acid;

6-methyl-3-phenyl-7-trans-[2-(4-methyl-phenyl)-ethenyl]-5-oxo-5H-thiazolo[3,2-a]pyrimidine-2-carboxylic acid;

6-chloro-3-phenyl-7-trans-(2-phenyl-ethenyl)-5-oxo-5H-thiazolo[3,2-a]pyrimidine-2-carboxylic acid;

6-chloro-3-phenyl-7-trans-[2-(2-methyl-phenyl)-ethenyl]-5-oxo-5H-thiazolo[3,2-a]pyrimidine-2-carboxylic acid;

6-chloro-3-phenyl-7-trans-[2-(3-methyl-phenyl)-ethenyl]-5-oxo-5H-thiazolo[3,2-a]pyrimidine-2-carboxylic acid;

6-chloro-3-phenyl-7-trans-[2-(4-methyl-phenyl)-ethenyl]-5-oxo-5H-thiazolo[3,2-a]pyrimidine-2-carboxylic acid;

6-chloro-3-phenyl-7-trans-[2-(2,5-dimethyl-phenyl)-ethenyl]-5-oxo-5H-thiazolo[3,2-a]pyrimidine-2-carboxylic acid;

6-methyl-3-phenyl-7-trans-[2-(3-methyl-phenyl)-ethenyl]-5-oxo-5H-thiazolo[3,2-a]pyrimidine-2-carboxylic acid;

6-methyl-3-phenyl-7-trans-[2-(2,5-dimethyl-phenyl)-ethenyl]-5-oxo-5H-thiazolo[3,2-a]pyrimidine-2-carboxylic acid;

6-methyl-3-phenyl-7-trans-(2-phenyl-ethenyl)-5-oxo-5H-thiazolo[3,2-a]pyrimidine-2-carboxylic acid;

3,6-dimethyl-7-trans-[2-(3-pyridyl)-ethenyl]-5-oxo-5H-thiazolo[3,2-a]pyrimidine-2-carboxylic acid;

6-methyl-3-phenyl-7-trans-[2-(3-pyridyl)-ethenyl]-5-oxo-5H-thiazolo[3,2-a]pyrimidine-2-carboxylic acid;

6-chloro-3-methyl-7-trans-[2-(3-pyridyl)-ethenyl]-5-oxo-5H-thiazolo[3,2-a]pyrimidine-2-carboxylic acid;

6-chloro-3-(4-chloro-phenyl)-7-trans-(2-phenyl-ethenyl)-5-oxo-5H-thiazolo[3,2-a]pyrimidine-2-carboxylic acid;

6-chloro-3-(4-methyl-phenyl)-7-trans-(2-phenyl-ethenyl)-5-oxo-5H-thiazolo[3,2-a]pyrimidine-2-carboxylic acid;

6-chloro-3-phenyl-7-trans-[2-(3-pyridyl)-ethenyl]-5-oxo-5H-thiazolo[3,2-a]pyrimidine-2-carboxylic acid;

6-chloro-3-(4-chloro-phenyl)-7-trans-[2-(2-methyl-phenyl)-ethenyl]-5-oxo-5H-thiazolo[3,2-a]pyrimidine-2-carboxylic acid;

6-chloro-3-(4-methyl-phenyl)-7-trans-[2-(2-methyl-phenyl)-ethenyl]-5-oxo-5H-thiazolo[3,2-a]pyrimidine-2-carboxylic acid;

6-chloro-3-(4-methoxy-phenyl)-7-trans-[2-(2-methyl-phenyl)-ethenyl]-5-oxo-5H-thiazolo[3,2-a]pyrimidine-2-carboxylic acid;

6-chloro-3-(4-chloro-phenyl)-7-trans-[2-(3-methyl-phenyl)-ethenyl]-5-oxo-5H-thiazol[3,2-a]pyrimidine-2-carboxylic acid;

6-chloro-3-(4-methyl-phenyl)-7-trans-[2-(3-methyl-phenyl)-ethenyl]-5-oxo-5H-thiazolo[3,2-a]pyrimidine-2-carboxylic acid;

6-chloro-3-(4-methoxy-phenyl)-7-trans-[2-(3-methyl-phenyl)-ethenyl]-5-oxo-5H-thiazolo[3,2-a]pyrimidine-2-carboxylic acid;

6-methyl-3-(4-methyl-phenyl)-7-trans-[2-(3-methyl-phenyl)-ethenyl]-5-oxo-5H-thiazolo[3,2-a]pyrimidine-2-carboxylic acid;

3-(4-chloro-phenyl)-6-methyl-7-trans-[2-(3-methyl-phenyl)-ethenyl]-5-oxo-5H-thiazolo[3,2-a]pyrimidine-2-carboxylic acid;

6-chloro-3-(4-methoxy-phenyl)-7-trans-(2-phenyl-ethenyl)-5-oxo-5H-thiazolo[3,2-a]pyrimidine-2-carboxylic acid;

3-(4-methoxy-phenyl)-6-methyl-7-trans-[2-(3-methyl-phenyl)-ethenyl]-5-oxo-5H-thiazolo[3,2-a]pyrimidine-2-carboxylic acid;

6-chloro-3-(4-methyl-phenyl)-7-trans-[2-(4-methyl-phenyl)-ethenyl]-5-oxo-5H-thiazolo[3,2-a]pyrimidine-2-carboxylic acid;

6-chloro-3-(4-chloro-phenyl)-7-trans-[2-(4-methyl-phenyl)-ethenyl]-5-oxo-5H-thiazolo[3,2-a]pyrimidine-2-carboxylic acid; and 6-chloro-3-(4-methoxy-phenyl)-7-trans-[2-(4-methyl-phenyl)-ethenyl]-5-oxo-5H-thiazolo[3,2-a]pyrimidine-2-carboxylic acid.

EXAMPLE 10

By proceeding according to Examples 7, 8 and 9, starting from 4-pyridyl-2-amino-thiazole-5-carboxylic acid esters and suitable acetoacetates, and using suitable heteroaromatic aldehydes, the following compounds were prepared:

3-(3-pyridyl)-7-trans-[2-(4-methyl-phenyl)-ethenyl]-5-oxo-5H-thiazolo[3,2-a]pyrimidine-2-carboxylic acid;

3-(3-pyridyl)-7-trans-[2-(3-methyl-phenyl)-ethenyl]-5-oxo-5H-thiazolo[3,2-a]pyrimidine-2-carboxylic acid;

6-methyl-3-(3-pyridyl)-7-trans-[2-(2-methyl-phenyl)-ethenyl]-5-oxo-5H-thiazolo[3,2-a]pyrimidine-2-carboxylic acid;

6-chloro-3-(3-pyridyl)-7-trans-(2-phenyl-ethenyl)-5-oxo-5H-thiazolo[3,2-a]pyrimidine-2-carboxylic acid;

6-methyl-3-(3-pyridyl)-7-trans-[2-(3-methyl-phenyl)-ethenyl]-5-oxo-5H-thiazolo[3,2-a]pyrimidine-2-carboxylic acid;

6-methyl-3-(3-pyridyl)-7-trans-[2-(4-methyl-phenyl)ethenyl]-5-oxo-5H-thiazolo[3,2-a]pyrimidine-2-carboxylic acid;

6-chloro-3-(3-pyridyl)-7-trans-[2-(3-methyl-phenyl)-ethenyl]-5-oxo-5H-thiazolo[3,2-a]pyrimidine-2-carboxylic acid;

6-chloro-3-(3-pyridyl)-7-trans-[2-(2-methyl-phenyl)-ethenyl]-5-oxo-5H-thiazolo[3,2-a]pyrimidine-2-carboxylic acid;

6-chloro-3-(3-pyridyl)-7-trans-[2-(4-methyl-phenyl)-ethenyl]-5-oxo-5H-thiazolo[3,2-a]pyrimidine-2-carboxylic acid; and 6-chloro-3-(3-pyridyl)-7-trans-[2-(2,5-dimethyl-phenyl)-ethenyl]-5-oxo-5H-thiazolo[3,2-a]pyrimidine-2-carboxylic acid.

EXAMPLE 11

7-chloromethyl-5-oxo-5H-thiazolo[3,2-a]pyrimidine-2-carboxylic acid, methyl ester (12.8 g), prepared according to Example 7, was dissolved in dimethylformamide and reacted with anhydrous potassium acetate (10 g) under stirring at room temperature for 20 hours. After dilution with ice water the precipitate was filtered and washed with water to give 7-acetoxymethyl-5-oxo-5H-thiazolo[3,2-a]pyrimidine-2-carboxylic acid, methyl ester (12.7 g) which was hydrolysed by treatment with 37% HCl (20 ml) in dioxane (100 ml) under stirring at room temperature for 2 hours. The reaction mixture was diluted with acetone and the precipitate was filtered and then treated with aqueous $Na_2HPO_4$: filtration and washings with water until neutral gave 7-hydroxymethyl-5-oxo-5H-thiazolo[3,2-a]pyrimidine-2-carboxylic acid, methyl ester (7.1 g) which was reacted with dicyclohexylcarbodiimide (14.01 g) in benzene (90 ml) and dimethylsulphoxide (40 ml) in the presence of trifluoroacetic acid (1 ml) and pyridine (1.71 ml) under stirring at room temperature for 20 hours. After treatment with oxalic acid bihydrate (3.1 g) at room temperature, the precipitate of dicyclohexylurea was filtered off and the organic solution was concentrated in vacuo to dryness: the residue was purified over a $SiO_2$ column using chloroform; methanol=95:5 as eluent. The 7-formyl-5-oxo-5H-thiazolo[3,2-a]pyrimidine-2-carboxylic acid, methyl ester so obtained (2.7 g) was reacted with triphenylphosphoniumbenzyl chloride (2.94 g) under treatment with 50% NaH (0.43 g) in dimethylsulfoxide (10 ml) and dichloroethane (6 ml) at room temperature for 18 hours. After evaporation of the solvent in vacuo, the residue was diluted with ice water and the precipitate was filtered and washed with water: crystallization from isopropyl alcohol gave 1.9 g of 7-trans-(2-phenyl-ethenyl)-5-oxo-5H-thiazolo[3,2-a]pyrimidine-2-carboxylic acid, methyl ester, m.p. 183°–185° C., which was hydrolyzed by treatment with 0.5% KOH solution in 95% ethanol (80 ml) at reflux temperature for 1 hour. The precipitate was filtered and dissolved in dimethylformamide-formic acid: the solution was then diluted with ice water. The precipitate was filtered and washed with water until neutral: crystallization from $CHCl_3$-isopropyl alcohol gave 1.3 g of 7-trans-(2-phenyl-ethenyl)-5-oxo-5H-thiazolo[3,2-a]pyrimidine-2-carboxylic acid, m.p. 246°–248° C., N.M.R. ($CF_3COOD$-$CDCl_3$) δ p.p.m.: 6.84 (s) (1H, C-6 proton), 7.12 (d) (1H, β-ethenyl proton), 7.45–7.74 (m) (5H, phenyl protons), 7.85 (d) (1H, α-ethenyl proton), 8.97 (s) (1H, C-3 proton), $J_{H\alpha H\beta}=16$ Hz.

EXAMPLE 12

6-ethyl-7-trans-(2-phenyl-ethenyl)-5-oxo-5H-thiazolo[3,2-a]pyrimidine-2-carboxylic acid (5.2 g) was reacted with thionyl chloride (3 ml) in dioxane (60 ml) at reflux temperature for 3 hours, then the mixture was evaporated in vacuo to dryness. The residue was reacted with excess of methanol at 50° C. for 30 minutes, then the solution was concentrated in vacuo and the residue was diluted with ice water. The precipitate was filtered and washed with water: crystallization from $CH_2Cl_2$-isopropyl ether gave 4.1 g of 6-ethyl-7-trans-(2-phenyl-ethenyl)-5-oxo-5H-thiazolo[3,2-a]pyrimidine-2-carboxylic acid, methyl ester, m.p. 214°–215° C.

By proceeding analogously the following compounds were prepared:
6-chloro-7-trans-(2-phenyl-ethenyl)-5-oxo-5H-thiazolo[3,2-a]pyrimidine-2-carboxylic acid, methyl ester;
6-methyl-7-trans-[2-(4-methyl-phenyl)-ethenyl]-5-oxo-5H-thiazolo[3,2-a]pyrimidine-2-carboxylic acid, ethyl ester;
6-methyl-7-trans-[2-(3-methyl-phenyl)-ethenyl]-5-oxo-5H-thiazolo[3,2-a]pyrimidine-2-carboxylic acid, ethyl ester;
6-chloro-7-trans-[2-(3-methyl-phenyl)-ethenyl]-5-oxo-5H-thiazolo[3,2-a]pyrimidine-2-carboxylic acid, ethyl ester;
6-chloro-7-trans-[2-(2-methyl-phenyl)-ethenyl]-5-oxo-5H-thiazolo[3,2-a]pyrimidine-2-carboxylic acid, ethyl ester;
6-chloro-7-trans-(2-phenyl-ethenyl)-5-oxo-thiazolo[3,2-a]pyrimidine-2-carboxylic acid, ethyl ester.

By proceeding analogously, the $C_1$–$C_4$ alkyl esters of the compounds described in the Examples 1 to 10 were prepared.

EXAMPLE 13

7-trans-[2-(3-pyridyl)-ethenyl]-5-oxo-5H-thiazolo[3,2-a]pyrimidine-2-carboxylic acid (1.9 g) was reacted with ethyl iodide (3 g) and anhydrous $K_2CO_3$ (1.75 g) under stirring at 60° C. for 6 hours. After cooling and dilution with ice water the precipitate was filtered and washed with water: crystallization from ethanol gave 1 g of 7-trans-[2-(3-pyridyl)-ethenyl]-5-oxo-5H-thiazolo[3,2-a]pyrimidine-2-carboxylic acid, ethyl ester, m.p. 193°–194° C.

EXAMPLE 14

6-methyl-7-trans-(2-phenyl-ethenyl)-5-oxo-5H-thiazolo[3,2-a]pyrimidine-2-carboxylic acid (1.1 g) was reacted with thionyl chloride (0.8 ml) in dioxane (30 ml) at reflux temperature for 3 hours, then the mixture was evaporated to dryness in vacuo.

The residue was dissolved in dioxane (30 ml) and reacted with 2-(diethylamino)-ethanol (1.13 g) at room temperature for 20 hours. After dilution with water the precipitate was filtered off, dissolved in acetone (40 ml) and treated with the stoichiometric amount of HCl in ether: the precipitate was filtered off, washed with ethyl acetate and dissolved in water.

Alkalization with $K_2CO_3$, filtration of the precipitate and crystallization from ether gave 0.5 g of 6-methyl-7-trans-(2-phenyl-ethenyl)-5-oxo-5H-thiazolo[3,2-a]pyrimidine-2-carboxylic acid, 2-(diethylamino)-ethyl ester, N.M.R. ($CDCl_3$-$CF_3COOD$) δ p.p.m.: 1.42 (s) [6H, —N($CH_2CH_3$)$_2$], 2.40 (s) (3H, —$CH_3$), 3.40 (q) [4H, —N($CH_2CH_3$)$_2$], 3.67 (m) (2H, —$OCH_2CH_2N$<), 4.84 (m) (2H, —$OCH_2CH_2N$<), 7.17 (d) (1H, β-ethenyl proton), 7.50 (m) (6H, α-ethenyl proton and phenyl protons), 8.90 (s) (1H, C-3 proton).

By proceeding analogously the following compounds were prepared:

6-methyl-7-trans-[2-(4-methyl-phenyl)-ethenyl]-5-oxo-5H-thiazolo[3,2-a]pyrimidine-2-carboxylic acid, 2-(diethylamino)-ethyl ester;

6-methyl-7-trans-[2-(3-methyl-phenyl)-ethenyl]-5-oxo-5H-thiazolo[3,2-a]pyrimidine-2-carboxylic acid, 2-(diethylamino)-ethyl ester;

6-chloro-7-trans-[2-(3-methyl-phenyl)-ethenyl]-5-oxo-5H-thiazolo[3,2-a]pyrimidine-2-carboxylic acid, 2-(diethylamino)-ethyl ester;

6-chloro-7-trans-[2-(2-methyl-phenyl)-ethenyl]-5-oxo-5H-thiazolo[3,2-a]pyrimidine-2-carboxylic acid, 2-(diethylamino)-ethyl ester;

6-chloro-7-trans-(2-phenyl-ethenyl)-5-oxo-5H-thiazolo[3,2-a]pyrimidine-2-carboxylic acid, 2-(diethylamino)-ethyl ester, m.p. 152°–155° C.;

6-chloro-7-trans-(2-phenyl-ethenyl)-5-oxo-5H-thiazolo[3,2-a]pyrimidine-2-carboxylic acid, 2-(dimethylamino)-ethyl ester;

6-methyl-7-trans-[2-(3-methyl-phenyl)-ethenyl]-5-oxo-5H-thiazolo[3,2-a]pyrimidine-2-carboxylic acid, 2-(dimethylamino)-ethyl ester;

6-methyl-7-trans-[2-(2,5-dimethyl-phenyl)-ethenyl]-5-oxo-5H-thiazolo[3,2-a]pyrimidine-2-carboxylic acid, 2-(diethylamino)-ethyl ester;

6-chloro-7-trans-[2-(4-methyl-phenyl)-ethenyl]-5-oxo-5H-thiazolo[3,2-a]pyrimidine-2-carboxylic acid, 2-(diethylamino)-ethyl ester; and 6-chloro-7-trans-[2-(2,5-dimethyl-phenyl)-ethenyl]-5-oxo-5H-thiazolo[3,2-a]pyrimidine-2-carboxylic acid, 2-(diethylamino)-ethyl ester.

By proceeding analogously, the di($C_1$–$C_2$)alkylamino-ethyl esters of the compounds described in the Examples 1 to 10 were prepared.

EXAMPLE 15

6-chloro-7-trans-(2-phenyl-ethenyl)-5-oxo-5H-thiazolo[3,2-a]pyrimidine-2-carboxylic acid, methyl ester, prepared according to Example 12 (1.1 g) was reacted with 2-amino-pyridine (0.85 g) in polyphosphoric acid (25 g) under stirring at 120° C. for 48 hours. After cooling, dilution with ice water and neutralization with 35% NaOH, the precipitate was filtered and washed with water: purification over a $SiO_2$ column using chloroform as eluant and then crystallization from $CH_2Cl_2$-methanol gave 0.4 g of 6-chloro-7-trans-(2-phenyl-ethenyl)-5-oxo-5H-thiazolo[3,2-a]pyrimidine-2-N-(2-pyridyl)-carboxamide, m.p. 305°–308° C., N.M.R. ($CDCl_3$-$CF_3COOD$) δp.p.m.: 7.30–8.30 (m) (11H; ethenyl protons, pyridyl protons and phenyl protons), 9.15 (s) (1H, C-3 proton).

By proceeding analogously the following compounds were prepared:

6-methyl-7-trans-[2-(3-methyl-phenyl)-ethenyl]-5-oxo-5H-thiazolo[3,2-a]pyrimidine-2-N-(2-pyridyl)-carboxamide;

6-chloro-7-trans-[2-(2-methyl-phenyl)-ethenyl]-5-oxo-5H-thiazolo[3,2-a]pyrimidine-2-N-(2-pyridyl)-carboxamide;

6-chloro-7-trans-[2-(3-methyl-phenyl)-ethenyl]-5-oxo-5H-thiazolo[3,2-a]pyrimidine-2-N-(2-pyridyl)-carboxamide;

6-methyl-7-trans-[2-(2-methyl-phenyl)-ethenyl]-5-oxo-5H-thiazolo[3,2-a]pyrimidine-2-N-(2-thiazolyl)-carboxamide;

6-methyl-7-trans-[2-(4-methyl-phenyl)-ethenyl]-5-oxo-5H-thiazolo[3,2-a]pyrimidine-2-N-(2-pyridyl)-carboxamide;

6-methyl-7-trans-[2-(2-methyl-phenyl)-ethenyl]-5-oxo-5H-thiazolo[3,2-a]pyrimidine-2-N-(2-pyridyl)-carboxamide;

6-methyl-7-trans-[2-(2,5-dimethyl-phenyl)-ethenyl]-5-oxo-5H-thiazolo[3,2-a]pyrimidine-2-N-(2-pyridyl)-carboxamide;

6-chloro-7-trans-[2-(2-methyl-phenyl)-ethenyl]-5-oxo-5H-thiazolo[3,2-a]pyrimidine-2-N-(2-thiazolyl)-carboxamide;

6-methyl-7-trans-[2-(2,4-dimethyl-phenyl)-ethenyl]-5-oxo-5H-thiazolo[3,2-a]pyrimidine-2-N-(2-pyridyl)-carboxamide;

6-chloro-7-trans-[2-(4-methyl-phenyl)-ethenyl]-5-oxo-5H-thiazolo[3,2-a]pyrimidine-2-N-(2-pyridyl)-carboxamide;

6-chloro-7-trans-[2-(2,5-methyl-phenyl)-ethenyl]-5-oxo-5H-thiazolo[3,2-a]pyrimidine-2-N-(2-pyridyl)-carboxamide;

6-chloro-7-trans-(2-phenyl-ethenyl)-5-oxo-5H-thiazolo[3,2-a]pyrimidine-2-N-(2-thiazolyl)-carboxamide;

6-methyl-7-trans-[2-(3-pyridyl)-ethenyl]-5-oxo-5H-thiazolo[3,2-a]pyrimidine-2-N-(2-pyridyl)-carboxamide; and 6-methyl-7-trans-[2-(3-pyridyl)-ethenyl]-5-oxo-5H-thiazolo[3,2-a]pyrimidine-2-N-(2-thiazolyl)-carboxamide.

EXAMPLE 16

6-chloro-2-chlorocarbonyl-7-trans-(2-phenyl-ethenyl)-5-oxo-5H-thiazolo[3,2-a]pyrimidine prepared according to Example 14 (2.4 g) was reacted with morpholine (2 g) in dioxane (60 ml) at room temperature for 2 hours. After evaporation of the solvent in vacuo, the residue was treated with aqueous $K_2CO_3$ and extracted with ethyl acetate: the organic phase was separated and evaporated in vacuo to dryness. The residue was crystallized from $CH_2Cl_2$-ethyl alcohol to give 1.7 g of 6-chloro-2-morpholinocarbonyl-7-trans-(2-phenyl-ethenyl)-5H-thiazolo[3,2-a]pyrimidine-5-one, m.p. 293°–295° C.

By proceeding analogously the following compounds were prepared:

6-methyl-7-trans-[2-(3-methyl-phenyl)-ethenyl]-5-oxo-5H-thiazolo[3,2-a]pyrimidine-2-N-(2-morpholino-ethyl)-carboxamide;

6-methyl-7-trans-[2-(3-methyl-phenyl)-ethenyl]-5-oxo-5H-thiazolo[3,2-a]pyrimidine-2-N-[2-(4-methyl-piperazin-1-yl)-ethyl]-carboxamide;

6-methyl-7-trans-[2-(3-methyl-phenyl)-ethenyl]-5-oxo-5H-thiazolo[3,2-a]pyrimidine-2-N-(2-piperidino-ethyl)-carboxamide;

6-chloro-7-trans-(2-phenyl-ethenyl)-5-oxo-5H-thiazolo[3,2-a]pyrimidine-2-N-(2-morpholino-ethyl)-carboxamide;

6-chloro-7-trans-(2-phenyl-ethenyl)-5-oxo-5H-thiazolo[3,2-a]pyrimidine-2-N-[2-(4-methyl-piperazin-1-yl)-ethyl]-carboxamide;

6-chloro-7-trans-(2-phenyl-ethenyl)-5-oxo-5H-thiazolo[3,2-a]pyrimidine-2-N-(2-piperidino-ethyl)-carboxamide;

6-chloro-7-trans-[2-(4-methyl-phenyl)-ethenyl]-5-oxo-5H-thiazolo[3,2-a]pyrimidine-2-N-(2-morpholino-ethyl)-carboxamide;

6-chloro-7-trans-[2-(2-methyl-phenyl)-ethenyl]-5-oxo-5H-thiazolo[3,2-a]pyrimidine-2-N-(2-morpholino-ethyl)-carboxamide;

6-chloro-7-trans-[2-(3-methyl-phenyl)-ethenyl]-5-oxo-5H-thiazolo[3,2-a]pyrimidine-2-N-(2-morpholino-ethyl)-carboxamide;

6-chloro-7-trans-[2-(2-methyl-phenyl)-ethenyl]-5-oxo-5H-thiazolo[3,2-a]pyrimidine-2-N-[2-(4-methyl-piperazin-1-yl)-ethyl]-carboxamide;

6-chloro-7-trans-[2-(3-methyl-phenyl)-ethenyl]-5-oxo-5H-thiazolo[3,2-a]pyrimidine-2-N-[2-(4-methyl-piperazin-1-yl)-ethyl]-carboxamide;

6-chloro-7-trans-[2-(3-methyl-phenyl)-ethenyl]-5-oxo-5H-thiazolo[3,2-a]pyrimidine-2-N-(2-piperidino-ethyl)-carboxamide;

6-chloro-2-morpholinocarbonyl-7-trans-[2-(3-methyl-phenyl)-ethenyl]-5H-thiazolo[3,2-a]pyrimidine-5-one;

6-chloro-2-morpholinocarbonyl-7-trans-[2-(2-methyl-phenyl)-ethenyl]-5H-thiazolo[3,2-a]pyrimidine-5-one;

6-chloro-2-morpholinocarbonyl-7-trans-[2-(4-methyl-phenyl)-ethenyl]-5H-thiazolo[3,2-a]pyrimidine-5-one;

6-chloro-2-morpholinocarbonyl-7-trans-[2-(2,5-dimethyl-phenyl)-ethenyl]-5H-thiazolo[3,2-a]pyrimidine-5-one;

6-methyl-2-morpholinocarbonyl-7-trans-[2-(2-methyl-phenyl)-ethenyl]-5H-thiazolo[3,2-a]pyrimidine-5-one;

6-methyl-2-morpholinocarbonyl-7-trans-[2-(3-methyl-phenyl)-ethenyl]-5H-thiazolo[3,2-a]pyrimidine-5-one;

6-methyl-2-morpholinocarbonyl-7-trans-[2-(4-methyl-phenyl)-ethenyl]-5H-thiazolo[3,2-a]pyrimidine-5-one;

6-methyl-2-morpholinocarbonyl-7-trans-[2-(2,5-dimethyl-phenyl)-ethenyl]-5H-thiazolo[3,2-a]pyrimidine-5-one;

6-chloro-2-piperidinocarbonyl-7-trans-(2-phenyl-ethenyl)-5H-thiazolo[3,2-a]pyrimidine-5-one;

6-cloro-2-[(4-methyl-piperazin-1-yl)-carbonyl]-7-trans-(2-phenyl-ethenyl)-5H-thiazolo[3,2-a]pyrimidine-5-one;

6-chloro-7-trans-(2-phenyl-ethenyl)-5-oxo-5H-thiazolo[3,2-a]pyrimidine-2-N-[(2-pyridyl)-methyl]-carboxamide;

6-methyl-7-trans-[2-(4-methyl-phenyl)-ethenyl]-5-oxo-5H-thiazolo[3,2-a]pyrimidine-2-N-[(2-pyridyl)-methyl]-carboxamide;

6-methyl-7-trans-[2-(3-methyl-phenyl)-ethenyl]-5-oxo-5H-thiazolo[3,2-a]pyrimidine-2-N-[(2-pyridyl)-methyl]-carboxamide;

6-chloro-7-trans-[2-(2-methyl-phenyl)-ethenyl]-5-oxo-5H-thiazolo[3,2-a]pyrimidine-2-N-[(2-pyridyl)-methyl]-carboxamide;

6-chloro-7-trans-[2-(3-methyl-phenyl)-ethenyl]-5-oxo-5H-thiazolo[3,2-a]pyrimidine-2-N-[(2-pyridyl)-methyl]-carboxamide;

6-chloro-7-trans-[2-(4-methyl-phenyl)-ethenyl]-5-oxo-5H-thiazolo[3,2-a]pyrimidine-2-N-[(2-pyridyl)-methyl]-carboxamide;

6-chloro-7-trans-[2-(2-methyl-phenyl)-ethenyl]-5-oxo-5H-thiazolo[3,2-a]pyrimidine-2-N-(1H-tetrazol-5-yl)-carboxamide;

6-methyl-7-trans-[2-(3-methyl-phenyl)-ethenyl]-5-oxo-5H-thiazolo[3,2-a]pyrimidine-2-N-(1H-tetrazol-5-yl)-carboxamide;

6-chloro-7-trans-[2-(3-methyl-phenyl)-ethenyl]-5-oxo-5H-thiazolo[3,2-a]pyrimidine-2-N-(1H-tetrazol-5-yl)-carboxamide;

6-chloro-7-trans-[2-(4-methyl-phenyl)-ethenyl]-5-oxo-5H-thiazolo[3,2-a]pyrimidine-2-N-(1H-tetrazol-5-yl)-carboxamide;

6-chloro-7-trans-[2-(2,5-dimethyl-phenyl)-ethenyl]-5-oxo-5H-thiazolo[3,2-a]pyrimidine-2-N-(1H-tetrazol-5-yl)-carboxamide;

6-methyl-7-trans-[2-(4-methyl-phenyl)-ethenyl]-5-oxo-5H-thiazolo[3,2-a]pyrimidine-2-N-(1H-tetrazol-5-yl)-carboxamide;

6-chloro-7-trans-(2-phenyl-ethenyl)-5-oxo-5H-thiazolo[3,2-a]pyrimidine-2-N-(1H-tetrazol-5-yl)-carboxamide, m.p. 285°–295° C. (dec.); and 6-methyl-7-trans-[2-(2,5-dimethyl-phenyl)-ethenyl]-5-oxo-5H-thiazolo[3,2-a]pyrimidine-2-N-(1H-tetrazol-5-yl)-carboxamide.

EXAMPLE 17

6,7-dimethyl-5-oxo-thiazolo[3,2-a]pyrimidine-2-carboxylic acid (2.65 g) was reacted with benzaldehyde (1.75 g) in methanol (60 ml) in the presence of sodium methylate (2.7 g) under stirring at reflux temperature for 96 hours.

After cooling and concentration in vacuo the precipitate was filtered and dissolved in a mixture of dimethylformamide and formic acid. The solution was diluted with ice water and the precipitate was filtered, washed with water until neutral and crystallized from isopropyl alcohol to give 1.8 g of 6-methyl-7-trans-(2-phenyl-ethenyl)-5-oxo-5H-thiazolo[3,2-a]pyrimidine-2-carboxylic acid, m.p. 257°–259° C.

EXAMPLE 18

6-chloro-2-chlorocarbonyl-7-trans-(2-phenyl-ethenyl)-5-oxo-5H-thiazolo[3,2-a]pyrimidine prepared according to Example 14 (3.5 g) was reacted with N-(2-hydroxy-ethyl)-morpholine (4.3 g) in dioxane (200 ml) at room temperature for 18 hours.

After evaporation of the solvent in vacuo the residue was treated with aqueous $NaHCO_3$ and extracted with ethyl acetate: the organic phase was separated and evaporated in vacuo to dryness. The residue was crystallized from $CH_2Cl_2$-isopropyl ether to give 2.7 g of 6-chloro-7-trans-(2-phenyl-ethenyl)-5-oxo-5H-thiazolo[3,2-a]-pyrimidine-2-carboxylic acid, 2-morpholino-ethyl ester, m.p. 177°–182° C., NMR ($CDCl_3$) $\delta$ ppm: 2.57 (m) (4H, C-3 and C-5 morpholinyl protons), 2.74 (t) (2H, —COOCH$_2$CH$_2$N<), 3.71 (m) (4H, C-2 and C-6 morpholinyl protons), 4.48 (t) (2H, —COOCH$_2$CH$_2$N<), 7.3–7.7 (m) (6H, $\beta$-ethenyl proton and phenyl protons), 7.91 (d) (1H, $\alpha$-ethenyl proton), 8.44 (s) (1H, C-3 proton).

By proceeding analogously the following compounds were prepared:

6-methyl-7-trans-[2-(2-methyl-phenyl)-ethenyl]-5-oxo-5H-thiazolo[3,2-a]pyrimidine-2-carboxylic acid, 2-morpholino-ethyl ester;

6-methyl-7-trans-[2-(3-methyl-phenyl)-ethenyl]-5-oxo-5H-thiazolo[3,2-a]pyrimidine-2-carboxylic acid, 2-morpholino-ethyl ester;

6-chloro-7-trans-[2-(3-methyl-phenyl)-ethenyl]-5-oxo-5H-thiazolo[3,2-a]pyrimidine-2-carboxylic acid, 2-morpholino-ethyl ester;

6-chloro-7-trans-[2-(2-methyl-phenyl)-ethenyl]-5-oxo-5H-thiazolo[3,2-a]pyrimidine-2-carboxylic acid, 2-morpholino-ethyl ester;

6-chloro-7-trans-(2-phenyl-ethenyl)-5-oxo-5H-thiazolo[3,2-a]pyrimidine-2-carboxylic acid, 2-piperidino-ethyl ester;

6-chloro-7-trans-(2-phenyl-ethenyl)-5-oxo-5H-thiazolo[3,2-a]pyrimidine-2-carboxylic acid, 2-(N-pyrrolidinyl)-ethyl ester;

6-chloro-7-trans-(2-phenyl-ethenyl)-5-oxo-5H-thiazolo[3,2-a]pyrimidine-2-carboxylic acid, 2-(2-methyl-morpholino)-ethyl ester;

6-chloro-7-trans-(2-phenyl-ethenyl)-5-oxo-5H-thiazolo[3,2-a]pyrimidine-2-carboxylic acid, 2-(cis-2,6-dimethyl-morpholino)-ethyl ester;

6-methyl-7-trans-[2-(4-methyl-phenyl)-ethenyl]-5-oxo-5H-thiazolo[3,2-a]pyrimidine-2-carboxylic acid, 2-morpholino-ethyl ester;

6-methyl-7-trans-[2-(2,5-dimethyl-phenyl)-ethenyl]-5-oxo-5H-thiazolo[3,2-a]pyrimidine-2-carboxylic acid, 2-morpholino-ethyl ester;

6-chloro-7-trans-[2-(2,5-dimethyl-phenyl)-ethenyl]-5-oxo-5H-thiazolo[3,2-a]pyrimidine-2-carboxylic acid, 2-morpholino-ethyl ester;

6-chloro-7-trans-[2-(4-methyl-phenyl)-ethenyl]-5-oxo-5H-thiazolo[3,2-a]pyrimidine-2-carboxylic acid, 2-morpholino-ethyl ester;

6-chloro-7-trans-(2-phenyl-ethenyl)-5-oxo-5H-thiazolo[3,2-a]pyrimidine-2-carboxylic acid, (3-pyridyl)-methyl ester, m.p. 221°–223° C.;

6-chloro-7-trans-[2-(4-methyl-phenyl)-ethenyl]-5-oxo-5H-thiazolo[3,2-a]pyrimidine-2-carboxylic acid, (3-pyridyl)-methyl ester;

6-methyl-7-trans-[2-(3-methyl-phenyl)-ethenyl]-5-oxo-5H-thiazolo[3,2-a]pyrimidine-2-carboxylic acid, (3-pyridyl)-methyl ester;

6-chloro-7-trans-[2-(2-methyl-phenyl)-ethenyl]-5-oxo-5H-thiazolo[3,2-a]pyrimidine-2-carboxylic acid, (3-pyridyl)-methyl ester; and 6-chloro-7-trans-[2-(3-methyl-phenyl)-ethenyl]-5-oxo-5H-thiazolo[3,2-a]pyrimidine-2-carboxylic acid, (3-pyridyl)-methyl ester.

By proceeding analogously the 2-morpholino-ethyl esters and the (3-pyridyl)-methyl esters of the compounds described in the Examples 1 to 10 were prepared.

EXAMPLE 19

6-chloro-7-trans-[2-(4-nitro-phenyl)-ethenyl]-5-oxo-5H-thiazolo[3,2-a]pyrimidine-2-carboxylic acid, methyl ester (3.82 g) was reacted with SnCl$_2$.2H$_2$O (25 g) in 37% HCl (15 ml) and acetic acid (45 ml) under stirring at 60° C. for 2 hours. After cooling the precipitate was filtered, washed with acetic acid and then suspended under stirring in 2.5% aqueous NaHCO$_3$; the product was filtered and washed with water until neutral to give 6-chloro-7-trans-[2-(4-amino-phenyl)-ethenyl]-5-oxo-5H-thiazolo[3,2-a]pyrimidine-2-carboxylic acid, methyl ester (2.54 g), which was treated under stirring with 1% KOH in 95% ethanol solution (90 ml) at reflux temperature for 6 hours. After cooling the precipitated potassium salt was collected by filtration and washed with methanol. Then the product was crystallized from formic acid-ethanol to give 1.72 g of 6-chloro-7-trans-[2-(4-amino-phenyl)-ethenyl]-5-oxo-5H-thiazolo[3,2-a]pyrimidine-2-carboxylic acid, m.p. 305°–315° C. (dec.).

By proceeding analogously, the following compound was prepared:

6-methyl-7-trans-[2-(4-amino-phenyl)-ethenyl]-5-oxo-5H-thiazolo[3,2-a]pyrimidine-2-carboxylic acid.

EXAMPLE 20

6-chloro-7-trans-(2-phenyl-ethenyl)-5-oxo-5H-thiazolo[3,2-a]pyrimidine-2-carboxylic acid (3 g) was dissolved in the stoichiometric amount of 4N NaOH by heating at 80° C. After cooling and dilution with acetone (100 ml) the precipitate was filtered and washed with acetone: 2.85 g of 6-chloro-7-trans-(2-phenyl-ethenyl)-5-oxo-5H-thiazolo[3,2-a]pyrimidine-2-carboxylic acid, sodium salt m.p. >300° C., were obtained.

EXAMPLE 21

Tablets, each weighing 150 mg and containing 50 mg of the active substance are manufactured as follows:

Compositions (for 10000 tablets)

6-chloro-7-trans-[2-(2-methyl-phenyl)-ethenyl]-5-oxo-5H-thiazolo[3,2-a]pyrimidine-2-carboxylic acid: 500 g
Lactose: 710 g
Corn starch: 237.5 g
Talc powder: 37.5 g
Magnesium stearate: 15 g 6-chloro-7-trans-[2-(2-methyl-phenyl)-ethenyl]-5-oxo-5-H-thiazolo[3,2-a]pyrimidine-2-carboxylic acid, lactose and a half of the corn starch are mixed; the mixture is then forced through a sieve of 0.5 mm openings. Corn starch (18 g) is suspended in warm water (180 ml). The resulting paste is used to granulate the powder. The granules are dried, comminuted on a sieve of sieve size 1.4 mm, then the remaining quantity of starch, talc and magnesium stearate is added, carefully mixed, and processed into tablets using punches of 8 mm diameter.

By proceeding analogously tablets were prepared having the same composition, but containing as active substance the following compounds:

6-chloro-7-trans-(2-phenyl-ethenyl)-5-oxo-5H-thiazolo[3,2-a]pyrimidine-2-carboxylic acid;

6-chloro-7-trans-[2-(3-methyl-phenyl)-ethenyl]-5-oxo-5H-thiazolo[3,2-a]pyrimidine-2-carboxylic acid;

6-methyl-7-trans-[2-(3-methyl-phenyl)-ethenyl]-5-oxo-5-thiazolo[3,2-a]pyrimidine-2-carboxylic acid; and 6-chloro-7-trans-[2-(4-methyl-phenyl)-ethenyl]-5-oxo-5H-thiazolo[3,2-a]pyrimidine-2-carboxylic acid.

EXAMPLE 22

Aerosol formulation 6-chloro-7-trans-[2-(2-methyl-phenyl)-ethenyl]-5-oxo-5H-thiazolo[3,2-a]pyrimidine-2-carboxylic acid: 2%
Ethanol: 10%
Lecithin: 0.2%
Mixture of dichlorofluoroethane and dichlorotetrafluoroethane (70:30 mixture) to: 100%

We claim:

1. A compound of formula (I)

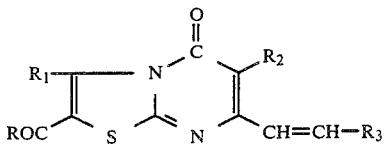 (I)

wherein
R is
(a) hydroxy;
(b) a $C_1$–$C_6$ alkoxy group unsubstituted or substituted by a

group, wherein each of $R_4$ and $R_5$ independently is a hydrogen atom or a $C_1$–$C_6$ alkyl group, or $R_4$ and $R_5$, taken together with the nitrogen atom to which they are linked, form an unsubstituted N-pyrrolidinyl or morpholino ring;
$R_1$ is a hydrogen atom or $C_1$–$C_6$ alkyl;
$R_2$ is a hydrogen or a halogen atom or a $C_1$–$C_4$ alkyl group;
$R_3$ is a 2-,3- or 4-pyridyl ring, each of which is unsubstituted or substituted by $C_1$–$C_6$ alkyl; or $R_3$ is a group of formula

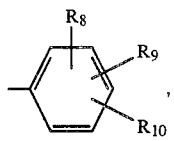

wherein each of $R_8$, $R_9$ and $R_{10}$ independently represents hydrogen, halogen, trihalo-$C_1$–$C_6$-alkyl, $C_3$–$C_4$-alkenyloxy, or a -(0)$_p$-$R_{11}$ group, wherein p is zero or 1 and $R_{11}$ represents a $C_1$–$C_6$ alkyl group, and the pharmaceutically acceptable salts thereof.

2. A compound of formula (I), according to claim 1, wherein
R is hydroxy, $C_1$–$C_4$ alkoxy, di($C_1$–$C_2$ alkyl)aminoethoxy;
$R_1$ is hydrogen;
$R_2$ is hydrogen, chlorine, bromine or $C_1$–$C_3$ alkyl; and
$R_3$ is
(a") a phenyl group unsubstituted or substituted by one or two substituents chosen from the group including fluorine, chlorine, $C_1$–$C_4$ alkyl, and $C_1$–$C_4$ alkoxy;
(b") a 2-, 3- or 4-pyridyl group, each of which unsubstituted or substituted by a methyl group; and the pharmaceutically acceptable salts thereof.

3. A compound selected from the group consisting of:
6-chloro-7-trans-(2-phenyl-ethenyl)-5-oxo-5H-thiazolo[3,2-a]pyrimidine-2-carboxylic acid;
6-methyl-7-trans-[2-(2-methyl-phenyl)-ethenyl]-5-oxo-5H-thiazolo[3,2-a]pyrimidine-2-carboxylic acid;
6-methyl-7-trans-[2-(4-methyl-phenyl)-ethenyl]-5-oxo-5H-thiazolo[3,2-a]pyrimidine-2-carboxylic acid;
6-methyl-7-trans-[2-(3-pyridyl)-ethenyl]-5-oxo-5H-thiazolo[3,2-a]pyrimidine-2-carboxylic acid;
6-methyl-7-trans-[2-(3-methyl-phenyl)-ethenyl]-5-oxo-5H-thiazolo[3,2-a]pyrimidine-2-carboxylic acid;
6-methyl-7-trans-[2-(4-ethoxy-phenyl)-ethenyl]-5-oxo-5H-thiazolo[3,2-a]pyrimidine-2-carboxylic acid;
6-chloro-7-trans-[2-(3-methyl-phenyl)-ethenyl]-5-oxo-5H-thiazolo[3,2-a]pyrimidine-2-carboxylic acid;
6-chloro-7-trans-[2-(2-methyl-phenyl)-ethenyl]-5-oxo-5H-thiazolo[3,2-a]pyrimidine-2-carboxylic acid;
6-chloro-7-trans-[2-(2,4-dimethyl-phenyl)-ethenyl]-5-oxo-5H-thiazolo[3,2-a]pyrimidine-2-carboxylic acid;
6-chloro-3-phenyl-7-trans-(2-phenyl-ethenyl)-5-oxo-5H-thiazolo[3,2-a]pyrimidine-2-carboxylic acid;
6-chloro-3-methyl-7-trans-(2-phenyl-ethenyl)-5-oxo-5H-thiazolo[3,2-a]pyrimidine-2-carboxylic acid;
6-chloro-7-trans-[2-(4-methyl-phenyl)-ethenyl]-5-oxo-5H-thiazolo[3,2-a]pyrimidine-2-carboxylic acid;
6-chloro-7-trans-[2-(4-fluoro-phenyl)-ethenyl]-5-oxo-5H-thiazolo[3,2-a]pyrimidine-2-carboxylic acid;
6-bromo-7-trans-(2-phenyl-ethenyl)-5-oxo-5H-thiazolo[3,2-a]pyrimidine-2-carboxylic acid;
6-chloro-7-trans-[2-(2-methoxy-3-ethoxy-phenyl)-ethenyl]-5-oxo-5H-thiazolo[3,2-a]pyrimidine-2-carboxylic acid;
6-chloro-7-trans-[2-(2,5-dimethyl-phenyl)-ethenyl]-5-oxo-5H-thiazolo[3,2-a]pyrimidine-2-carboxylic acid;
6-chloro-7-trans-[2-(4-chloro-phenyl)-ethenyl]-5-oxo-5H-thiazolo[3,2-a]pyrimidine-2-carboxylic acid;
6-methyl-7-trans-[2-(2,4-dimethyl-phenyl)-ethenyl]-5-oxo-5H-thiazolo[3,2-a]pyrimidine-2-carboxylic acid;
6-methyl-7-trans-[2-(2-methoxy-3-ethoxy-phenyl)-ethenyl]-5-oxo-5H-thiazolo[3,2-a]pyrimidine-2-carboxylic acid;
6-methyl-7-trans-[2-(2,5-dimethyl-phenyl)-ethenyl]-5-oxo-5H-thiazolo[3,2-a]pyrimidine-2-carboxylic acid;
6-methyl-7-trans-[2-(2,6-dichloro-phenyl)-ethenyl]-5-oxo-5H-thiazolo[3,2-a]pyrimidine-2-carboxylic acid;
6-methyl-7-trans-[2-(4-chloro-phenyl)-ethenyl]-5-oxo-5H-thiazolo[3,2-a]pyrimidine-2-carboxylic acid;
and the pharmaceutically acceptable salts thereof.

4. A pharmaceutical composition suitable for use as an anti-allergic agent, said composition comprising a therapeutically effective amount of a compound as claimed in claim 1, in association with a pharmaceutically acceptable carrier or diluent.

5. A pharmaceutical composition suitable for use as an anti-allergic agent, said composition comprising a therapeutically effective amount of a compound as claimed in claim 2, in association with a pharmaceutically acceptable carrier or diluent.

6. A pharmaceutical composition suitable for use as an anti-allergic agent, said composition comprising a therapeutically effective amount of a compound as claimed in claim 3, in association with a pharmaceutically acceptable carrier or diluent.

* * * * *

UNITED STATES PATENT AND TRADEMARK OFFICE
CERTIFICATE OF CORRECTION

PATENT NO. : 4,609,660

DATED : September 2, 1986

INVENTOR(S) : Doria et al

It is certified that error appears in the above-identified patent and that said Letters Patent is hereby corrected as shown below:

On the front page of the patent under the heading: "Related U.S. Application Data", delete 569,693, Jan. 11, 1985" and replace by --569,963, Jan. 11, 1984--

Column 1 line 6 delete "569,693" and replace by --569,963--

Column 1 line 7 delete "1985" and replace by --1984--

Signed and Sealed this

Third Day of March, 1987

*Attest:*

DONALD J. QUIGG

*Attesting Officer*  *Commissioner of Patents and Trademarks*